(12) United States Patent
Rosman et al.

(10) Patent No.: US 11,918,666 B2
(45) Date of Patent: Mar. 5, 2024

(54) TOPICAL FORMULATIONS COMPRISING STRONTIUM AND METHYLSULFONYLMETHANE (MSM) AND METHODS OF TREATMENT

(71) Applicant: NOON AESTHETICS M.R LTD., Tel-Aviv (IL)

(72) Inventors: Eran Rosman, Tel Aviv (IL); Masha Minkin, Tel Aviv (IL)

(73) Assignee: NOON AESTHETICS M.R LTD., Tel-Aviv (IL)

( * ) Notice: Subject to any disclaimer, the term of this patent is extended or adjusted under 35 U.S.C. 154(b) by 0 days.

(21) Appl. No.: 17/067,259

(22) Filed: Oct. 9, 2020

(65) Prior Publication Data

US 2021/0100725 A1 Apr. 8, 2021

Related U.S. Application Data

(63) Continuation-in-part of application No. PCT/IL2019/050386, filed on Apr. 4, 2019.

(60) Provisional application No. 62/654,540, filed on Apr. 9, 2018.

(51) Int. Cl.

| A61K 8/19 | (2006.01) |
| A61K 8/34 | (2006.01) |
| A61K 8/365 | (2006.01) |
| A61K 8/368 | (2006.01) |
| A61K 8/38 | (2006.01) |
| A61K 8/46 | (2006.01) |
| A61K 8/67 | (2006.01) |
| A61K 8/9789 | (2017.01) |
| A61K 31/10 | (2006.01) |
| A61K 33/14 | (2006.01) |
| A61K 33/24 | (2019.01) |
| A61Q 19/02 | (2006.01) |
| A61Q 19/08 | (2006.01) |
| A61Q 19/10 | (2006.01) |
| A61K 45/06 | (2006.01) |

(52) U.S. Cl.
CPC ............... *A61K 8/19* (2013.01); *A61K 8/347* (2013.01); *A61K 8/365* (2013.01); *A61K 8/368* (2013.01); *A61K 8/38* (2013.01); *A61K 8/463* (2013.01); *A61K 8/466* (2013.01); *A61K 8/671* (2013.01); *A61K 8/9789* (2017.08); *A61K 31/10* (2013.01); *A61K 33/14* (2013.01); *A61K 33/24* (2013.01); *A61Q 19/02* (2013.01); *A61Q 19/08* (2013.01); *A61Q 19/10* (2013.01); *A61K 45/06* (2013.01); *A61K 2800/10* (2013.01); *A61K 2800/75* (2013.01)

(58) Field of Classification Search
CPC ........................................................ A61K 8/19
See application file for complete search history.

(56) References Cited

U.S. PATENT DOCUMENTS

| 5,716,625 A | 2/1998 | Hahn et al. |
| 2003/0031727 A1 | 2/2003 | Hahn et al. |
| 2007/0270358 A1 | 11/2007 | de Paoliambrosi |
| 2008/0038219 A1 | 2/2008 | Mosbaugh et al. |
| 2010/0183741 A1* | 7/2010 | Mallard ............... A61K 31/12 |
| | | 514/390 |

FOREIGN PATENT DOCUMENTS

| EP | 2269615 B1 | 3/2018 |
| JP | H11502505 A | 3/1999 |
| JP | 2006521342 A | 9/2006 |
| JP | 2006525951 A | 11/2006 |
| WO | 2006002302 A1 | 1/2006 |

OTHER PUBLICATIONS

Webster. Combination of Azelaic Acid Therapy for Acne Vulgaris. Aug. 2000.*
"Equine America MSM & Zinc Ointment," Equestrian Products Online Store, Retrieved from URL: https://www.justequine.co.uk/products/horse-health-nutrition/external-applications/equine-america-msm-zinc-ointrnent/, Accessed on Aug. 30, 2016, 4 pages.
International Search Report and Written Opinion for International Application No. PCT/IL2019/050386, dated Jun. 16, 2019.
"The Many Health Benefits of MSM," BioNatures-Online store, Published on Jan. 4, 2018, Retrieved from URL: https://bionatures.com/blogs/news/the-many-health-benefits-of-msm, Accessed on Jun. 19, 2019, 7 pages.
"Double White-hydroquinone," May 2020, pp. 1-8.
European Patent Application No. 19785230.4, Extended European Search Report dated Dec. 3, 2021, 14 pages.
Hahn G.S., et al., "Strontium Is a Potent and Selective Inhibitor of Sensory Irritation," Dermatologic Surgery, Sep. 1999, vol. 25(9), pp. 689-694.
Indian Patent Application No. 202047043468, Office Action dated Mar. 7, 2022.
International Preliminary Report on Patentability for International Application No. PCT/IL2019/050386, dated Oct. 22, 2020, 10 pages.
Singapore office action for Patent Application 11202009799Q dated Apr. 4, 2022.
Japanese Office Action, Chinese Patent Application JP2020555348, dated Dec. 20, 2022. (With Translation).

* cited by examiner

*Primary Examiner* — Sarah Alawadi
(74) *Attorney, Agent, or Firm* — BROWDY AND NEIMARK, PLLC

(57) ABSTRACT

A topical cosmetic or medicinal formulation comprising strontium and methylsulfonylmethane (MSM) reduces irritation that may be caused by skin treatment compositions, especially low-pH skin treatments. strontium and methylsulfonylmethane may be provided with a dermatologically acceptable carrier as a separate composition, or may be provided with other active ingredients in a skin treatment formulation.

18 Claims, 5 Drawing Sheets

TOPICAL FORMULATIONS COMPRISING STRONTIUM AND METHYLSULFONYLMETHANE (MSM) AND METHODS OF TREATMENT

CROSS-REFERENCE TO RELATED APPLICATIONS

The present application is a continuation-in-part of International Application Number PCT/IL2019/050386, filed Apr. 4, 2019, which claims benefit of Provisional Application U.S. 62/654,540, filed April 2018. The entire contents of each of the above-identified applications are hereby incorporated herein by reference.

FIELD OF THE INVENTION

The current disclosure relates generally to topical formulations comprising Strontium and Methylsulfonylmethane (MSM) and methods of treatment.

BACKGROUND

Using high concentration of active ingredients in topical cosmetic and medicinal products produce desired results usually when a low pH is used, which may cause side effects, such as irritation,—including stinging, burning, itching, edema, other unpleasant sensations, redness, etc.

SUMMARY

In one aspect, the present disclosure relates to a composition comprising a combination of: strontium; methylsulfonylmethane; and a physiologically acceptable carrier.

In a further aspect, the present disclosure relates to formulation comparing a composition that comprises a combination of strontium and methylsulfonylmethane. The disclosed formulation may be a topical cosmetic or medicinal formulation comprising. In another aspect, the present disclosure relates a method of cosmetic or therapeutic treatment, comprising administration of composition comprising strontium, MSM and a dermatologically or a formulation comprising same, wherein wherein the combination of strontium and MSM provides a synergistic effect in the cosmetic or therapeutic treatment as compared to the effect provided by strontium and MSM each alone.

In still another aspect, the present disclosure relates to a method of reducing skin irritant effects of a topical cosmetic or medicinal formulation or other chemical irritants, comprising administrating to a subject in need thereof of a composition comprising strontium and MSM, preferably but not exclusively, in a cosmetic or medicinal formulation.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
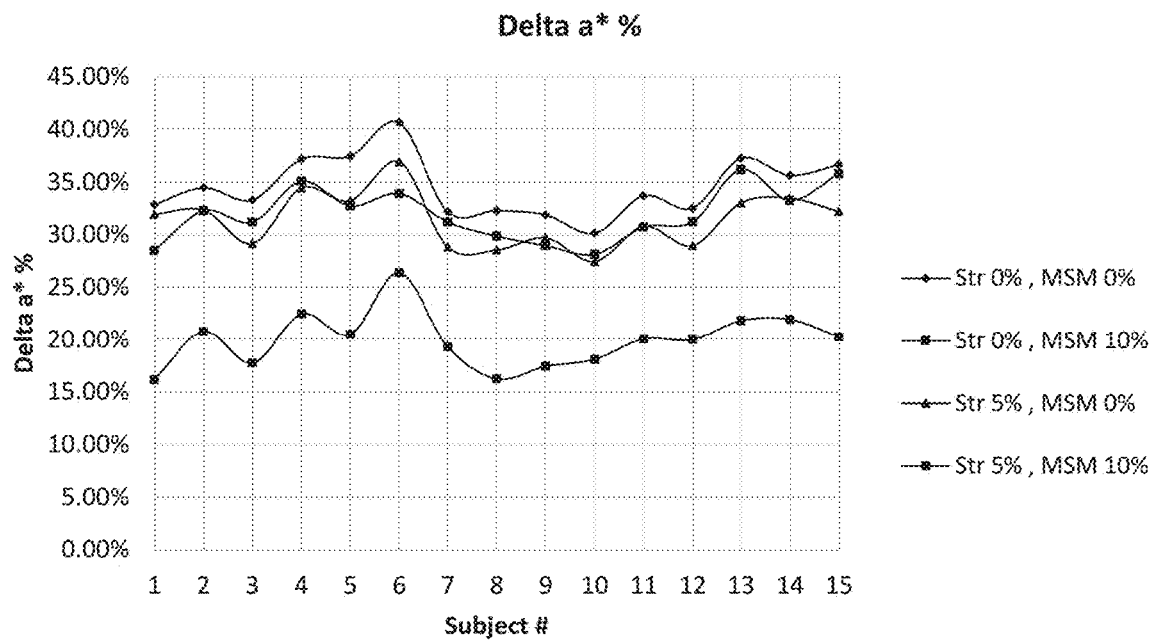
FIG. 1 depicts comparative clinical data from Example 1 showing an effect on skin redness (delta a*) with formulations according to the disclosure.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present disclosure may be practiced without these specific details. In other instances, well-known methods, procedures, and components have not been described in detail so as not to obscure the present disclosure.

Embodiments of the disclosure are directed to formulations comprising Strontium and methylsulfonylmethane (MSM). The combination of Strontium and methylsulfonylmethane (MSM) may be referred to in the application as "the combination".

Further embodiments of the disclosure are directed to methods of treating or preventing stinging, itching, burning, erythema and other sensations and feelings, and their development, associated with skin irritant products, chemicals, processes and other reasons of irritation or such feelings, with change of temperatures, with burns or with change of pH, wherein the method comprises administering a formulation comprising Strontium and Methylsulfonylmethane (MSM).

The present disclosure relates to the surprising discovery that the combination of strontium with methylsulfonylmethane (MSM) in a topical product(s) formulation is useful in reducing the development, incidence and severity of irritation and erythema associated with topically applied skin irritants, including irritation and neurogenic inflammations caused by various ingredients of skin treatment products.

This effect of strontium with methylsulfonylmethane (MSM) is a synergistic effect. The synergistic effect is characterized by the combination of two materials having a stronger effect than the simple sum of the effect of each material. This is further illustrated in the example section below and in tables 1 and 2.

The synergistic effect also enables the use of small amounts of strontium MSM which are not effective or have a very low effect on their own.

In one aspect, the present disclosure relates to a composition comprising a combination of strontium, methylsulfonylmethane and a physiologically acceptable carrier.

In a further aspect, embodiments of the present disclosure relate to unique and efficient aesthetic and pharmaceutic formulations (products) for skin care and treatment, the uniqueness over common corresponding skin care products being attributed, at least in part, to combining with, or incorporating into these formulations a composition comprising the contemplated combination of strontium and MSM. This combination confers or bestows to the disclosed formulations the ability to offer the most effective skin treatment without common side effects, such as irritation, burning, redness and unpleasant sensation during use. A disclosed formulation contains active ingredients at breakthrough high concentration levels applicable for various skin problems, such as aging skin, hyper-pigmentation, sun damage and loss of elasticity, blemishes, seborrhea, and more, without the typical aftereffects.

Thus, the contemplated composition combining strontium and MSM and a formulation comprising this composition or provided together therewith enables using high concentration of active ingredients, e.g., in cosmetic products, usually with a low pH, without the typical irritations and side effects (redness etc.) resulting from the chemical irritant or the low pH.

The combination of strontium and MSM can be used in a formulation and/or product comprising an active cosmetic or a therapeutic ingredient, or used prior or post the use of a topical cosmetic or therapeutic product or prior or post performing a treatment to the skin (for example, laser treatment or other treatments) or post sun exposure or post burns. When the combination is not part of the product and is applied before or after the product or treatment or sun exposure, the combination should be used in close proximity timewise in order to have the desired effect of reducing irritation and erythema. This disclosure enables more efficacious products for the treatment of the skin, without the typical side effects: redness, itching, burning, stinging, etc. The effectiveness of the products is increased because the subject is more likely to use the product as prescribed if there are no side effects or the side effects are mild. In addition, the aesthetician/doctor administering/applying a treatment is more likely to keep the products on for longer if the customer/patient is not suffering or uncomfortable. For example, one can leave a chemical peel on the treated area for longer, if there is less irritation, and thus receive the full effectiveness that is embodied in the product. In addition, it enables the subject or the practitioner to increase the amount of active ingredient since the side effects of irritation and redness are eliminated or reduced.

In addition to reducing the side effects, the effectiveness of the active ingredients) is not harmed or compromised with the addition of strontium and MSM.

In some embodiments, the combination can be used for alleviating irritation and erythema associated with skin diseases such as atopic dermatitis, eczema, seborrhea, rosacea and psoriasis.

In some embodiments, the combination can be used for treating dry skin as a result of environment conditions such as "winter itch".

In some embodiments, the combination is used in products for treating acne.

In some embodiments, the combination is used in products for anti-aging.

In some embodiments, the strontium and MSM may be in separate products and are applied one after the other in order to achieve the desired effect of reducing irritation and erythema. In some embodiments, the strontium is applied and immediately afterwards MSM is applied. In some embodiments, the MSM is applied and immediately afterwards Strontium is applied.

In some embodiments, a disclosed formulation comprising a disclosed composition of strontium and MSM further comprises one or more additional active cosmetic or therapeutic ingredients.

In some embodiments, the additional active cosmetic or therapeutic ingredient is at least one of an alpha hydroxy acid (AHA) such as, but not limited to, glycolic acid, lactic acid, mandelic acid, tartaric acid, malic acid or citric acid; a beta hydroxy acid (BHA) such as, but not limited to, salicylic acid or citric acid; a retinoid such as retinol, retinoic acid or any other derivative of vitamin A; an alpha keto acid such as pyruvic acid; a dicarboxylic acid such as azelaic acid; arbutin such as alpha- or beta-arbutin; vitamin C and or a derivative thereof such as ascorbyl tetraisopalmitate or ascorbyl glucoside; benzoyl peroxide; sulfur; resorcinol, resorcinol monoacetate; hydroquinone; kojic acid; sodium laureth sulfate, disodium laureth sulfosuccinate; or medxtract Chamomile distilled.

An active agent in a disclosed cosmetic or therapeutic formulation may be present in any amount in the range of from 0.1% w/w to 70% w/w, depending on the type, duration and/or intended use of the formulation.

In one embodiment, the active ingredient is azelaic Acid.

In one embodiment, the active ingredient is glycolic acid.

In some embodiments, a contemplated formulation is a cosmetic formulation comprising a disclosed combination of Strontium and MSM in a topical product which is effective as cosmetic treatment to the skin, and supports skin soothing and calmness of the skin during treatment, and overall calmness of the skin, as well as providing a cosmetic effect to the skin, such as improving skin appearance. When topically applied to the skin, the combination improves the skin appearance.

For example, disclosed herein are face care products for in-clinic or home treatments, such as peels, ampoules and masks that are leave on face care products for use by adults on daily basis. Such products comprise, in accordance with the present disclosure, an acidic active agent such an alpha hydroxy acid (AHA), beta hydroxy acid (BHA) or both, and a combination of MSM and strontium in its salt form. Exemplary formulations for skin peeling and rejuvenation described in Example III herein.

The alpha hydroxy acid L(+)-lactic acid is a natural, functional metabolite in mammals, and serves as mammalian fuel. Lactic acid is found in nature in milk and in the skin. It has properties of exfoliation for skin rejuvenation. The safety of using lactic acid in cosmetic formulations has been assessed by the Cosmetic Ingredient Review (CIR) Expert Panel, an independent, non-profit scientific body, consisting of world-renowned scientists and physicians, and supported by the Food and Drug Administration (FDA) and the Consumer Federation of America (CFA). The CIR Expert Panel was established in order to thoroughly review and assess the safety of ingredients used in cosmetics. The CIR Expert Panel concluded that lactic acid is safe as used in cosmetics at concentrations ≤10% w/w, at final formulation pH ≥3.5, when formulated to avoid increasing sun sensitivity or when directions for use include the daily use of sun protection. Although lactic acid does not present a hazard for human health based on its low hazard profile, in terms of skin irritation and skin corrosivity, this AHA at concentrations >10% w/w is irritating and even corrosive to some skin types. Addition of a disclosed composition comprising MSM and strontium to face peeling products comprising lactic acid at concentrations >10% w/w, dramatically reduced the irritating or corroding effect of this acidic active ingredient.

Formulations contemplated by the present disclosure may comprise lactic acid in amounts that range from about 0.1% to about 40% w/w. For example, form about 0.5% to about 1.5% w/w, from about 1% to about 5% w/w, from about 3% to about 10% w/w, from about 5% to about 15% w/w, from about 10% to about 20% w/w, from about 15% to about 30% w/w, from about 10% to about 30% w/w or form about 10% to about 40% w/w, and any subranges and individual values therebetween.

Glycolic acid is a naturally occurring product, a constituent of sugar cane juice, permitted by US FDA for use as an indirect food additive in adhesives. The safety of glycolic acid has been assessed by the CIR Expert Panel, which concluded that this ingredient is safe for use in cosmetic products at concentrations ≤10% w/w, at final formulation pH≥3.5, when formulated to avoid increasing sun sensitivity or when directions for use include the daily use of sun protection.

Formulations contemplated by the present disclosure may comprise glycolic acid in amounts that range from about 0.1% to about 50% w/w. For example, form about 0.5% to about 2% w/w, from about 1% to about 5% w/w, from about 3% to about 10% w/w, from about 5% to about 15% w/w, from about 10% to about 20% w/w, from about 15% to about 30% w/w, from about 10% to about 30% w/w, form about 10% to about 40% w/w, or from about 10% to about 50% w/w, and any subranges and individual values therebetween.

The beta-hydroxy acid salicylic acid is a known keratolytic, anti-microbial and anti-inflammatory substance. When applied onto the skin, it promotes the elimination of dead cells and the regeneration of the epidermis. Two main applications of salicylic acid-containing products are skin purification and anti-aging. The human percutaneous absorption from topically applied 2% w/w salicylic acid containing products is in the range of 20% of the applied dose of salicylic acid.

Formulations contemplated herein may comprise salicylic acid in amounts that range from about 0.1% to about 50% w/w. For example, form about 0.5% to about 2% w/w, from about 1% to about 5% w/w, from about 3% to about 10% w/w, from about 5% to about 15% w/w, from about 10% to about 20% w/w, from about 15% to about 30% w/w, from about 10% to about 30% w/w, from about 1% to about 20% w/w, or from about 1% to about 50% w/w, and any subranges and individual values therebetween.

Further contemplated rejuvenating formulations may comprise at least one of mandelic acid, tartaric acid, malic acid, citric acid, azelaic acid, pyruvic acid and any combination thereof, in a total amount of from 0.1 to 70% w/w.

In some embodiments, a disclosed formulation is formulated as a cosmetic or therapeutic formulation for treatment of acne (herein also referred to as "anti-acne formulation"). Contemplated anti-acne formulations contain a composition comprising a combination of MSM and strontium, at least one anti-acne active agent and, optionally, also one or more anti-inflammatory active agents. For example, an anti-acne formulation may comprise one or more of azelaic acid, lactic acid, benzoyl peroxide, sulfur, resorcinol, and/or resorcinol monoacetate. Such formulations are useful for treating bumpy skin with papules and associated redness, helping to reduce discoloration. Exemplary formulations for treating acne are described in Example IV herein.

Azelaic acid, a dihydroxy acid ($HOOC(CH_2)_7COOH$), is a naturally occurring acid found in grains such as barley, wheat, and rye. It has diversified biological effects such as anti-bacterial, anti-inflammatory, anti-fungal, antioxidant and tyrosinase inhibitor. Having antimicrobial and anti-inflammatory properties makes azelaic acid effective in the treatment of skin conditions like acne and rosacea. The acid can prevent future outbreaks and clean bacteria from pores in the skin that cause acne, reduce inflammation so acne becomes less visible, less red, and less irritated, gently encouraging cell turnover so the skin heals more quickly and scarring is minimized.

The acid has some side effects, such as skin burning, dryness, and peeling. The safety of azelaic acid has been assessed by the CIR Expert Panel. For common cosmetic products, the CIR Expert Panel concluded that this ingredient is safe for use in cosmetics at concentrations up to 0.3% in leave-on and up to 10% in rinse-off products. Contemplated anti-acne formulation disclosed herein may contain up to 25% w/w azelaic acid and still be non-irritating.

For example, an anti-acne formulations may comprise azelaic acid in an amount of form about 0.1% to about 40% w/w, form about 0.1% to about 2% w/w, form about 1% to about 5% w/w, form about 4% to about 8% w/w, form about 5% w/w to about 10% w/w, form about 10% to about 20% w/w, form about 22% to about 28% w/w, form about 25% to about 30% w/w, or from about 10% to about 30% w/w, and any subranges and individual values therebetween.

Exemplary anti-acne formulation disclosed herein may comprise at least the following cosmetic and/or therapeutic active ingredients: (i) azelaic acid in an amount of form about 0.1% to about 40% w/w, form about 0.1% to about 5.0% w/w, form about 5.0% to about 15.0% w/w, or from about 10% to about 30% w/w; (i) lactic acid in an amount of from 10% to 20% w/w, for example, from about 11% to about 15% w/w; (iii) alpha-arbutin in an amount of from about 1.0% to about 20.0% w/w, for example, from about 2.0% to 8.0% w/w or from 5.0% to 10.0% w/w.

Formulations for treatment of acne encompassed by the present disclosure may further comprise additional or alternative active agents such as, but not limited to, benzoyl peroxide (in an amount of form about 0.1% to about 20% w/w, for example, from about 1.0% to about 10% w/w, or from about 5.0% to about 10% w/w), sulfur (in an amount of form about 0.1% to about 20% w/w, for example, from about 1.0% to about 10% w/w, or from about 5.0% to about 10% w/w), resorcinol, resorcinol monoacetate (in an amount of form about 0.1% to about 20% w/w, for example, from about 1.0% to about 10% w/w, or from about 5.0% to about 10% w/w).

Benzoyl peroxide is an organic peroxide having a structural formula $(ChH_5-C(=O)O-)_2$ (often abbreviated as $(BzO)_2$), a white granular crystalline solid with a faint odour of benzaldehyde. Benzoyl peroxide is an oxidizer which is used as a medication, as a bleach and water disinfectant, and as an important industrial chemical. As a medication, benzoyl peroxide is mostly used to treat acne, either alone or in combination with other treatment. Benzoyl peroxide works to treat and prevent acne by killing bacteria underneath the skin, as well as helping the pores shed dead skin cells and excess sebum (oil). This anti-acne active agent works particularly well for inflammatory acne, which is characterized by red bumps that contain pus (pustules, papules, cysts, and nodules) instead of whiteheads and blackheads.

1, 3-Benzenediol, also known as resorcin belongs to the class of organic compounds known as resorcinols, namely, compounds containing resorcinol moiety which is a benzene ring bearing two hydroxyl groups at positions 1 and 3. Resorcinol is used as a disinfectant or an antiseptic in pharmaceutical products. It is used to treat skin infections as seborrheic dermatitis, psoriasis, calluses, eczema, warts, and acne. Resorcinol acetate, a resorcinol derivative, is used as an ingredient to reduce the number of acne blemishes, acne pimples, blackheads, and whiteheads as well as for treatment of seborrheic dermatitis, eczema, psoriasis, and other skin disorders. In some embodiments, a disclosed formulation is formulated as a whitening or lightening formulation. The process of treating hyperpigmentation spots, also referred to herein as "whitening treatment", requires a regular and continuous use of a combination of whitening agents and lightening agents, which are specific ingredients that have an inhibiting effect on one or more of the processes that mediate the production and distribution of melanin in the skin. The whitening and lightening agents are also, collectively, referred to herein as "melanin inhibitors". Initial results of whitening and corrective processes are usually visible within two or three weeks after treatment commences, but more significant results in repairing and strengthening skin structure will be only achieved after several months, as the treatment continues. In case of deep and chronic spots, the treatment may need to be longer and combined with peeling treatment, for example, using any of the peeling formulations disclosed herein, in order to achieve effective results.

Melanin inhibitors used in embodiments of the present disclosure include, but are not limited to, alpha- or beta-arbutin, azelaic acid, kojic acid, niacinamide, hydroquinone, vitamin C and derivatives thereof, retinoids, lactic acid, peptides (e.g., Oligopeptide-68) and sun protection agents.

Alpha-arbutin is an extremely powerful whitening agent, acting as a melanin production inhibitor by inhibiting tyrosinase activity (an oxidizing enzyme that produces melanin) in all hyperpigmentation disorders. Although alpha-arbutin is a natural derivative of hydroquinone, this whitening agent doesn't possess any risks or side effects. There are two types of arbutin compound: alpha- and beta-arbutin. Both types are effective in lightening skin, but alpha arbutin is more potent and has stability and efficiency which are 50 times higher than beta-arbutin. Arbutin is effective for treating hyperpigmentation disorders in all Fitzpatrick skin phototypes and is safe for daily maintenance for an extended period of time, throughout the seasons.

Alpha-arbutin is used in cosmetic formulations to lighten skin pigmentation. For this purpose, up to 2% of alpha-Arbutin is used in finished cosmetic products for face/neck care, and up to 0.5% for body lotions.

Vitamin C and vitamin C derivatives, being tyrosinase inhibitors, have a skin whitening and lightening effects. For example, ascorbyl tetraisopalmitate—an oil-soluble vitamin C derivative, works as a powerful antioxidant and whitening agent, with both anti-acne and anti-aging capabilities. Ascorbyl glucoside is a natural water-soluble vitamin C (ascorbic acid) stabilized with glucose. Ascorbyl glucoside prevents pigmentation of the skin by suppressing melanin synthesis in melanocytes. In addition, it has the ability to reduce the amount of pre-existing melanin, resulting in a lighter pigmentation of the skin. Contemplated skin lightening formulation comprising 5% w/w ascorbyl glucoside are useful for whitening as well as for brightening dull looking skin and reversing the effects of aging.

In a concentration of 20% (and up), azelaic acid is able to reduce the production of the brown pigment melanin by inhibiting its production process (acts as a tyrosinase inhibitor). Azelaic acid has a unique attribute: it specifically affects areas that produce excess pigmentation and does not whiten areas with normal melanin production. In addition to whitening, azelaic acid has other anti-aging attributes such as skin renewal, rehabilitation, resuscitation and general maintenance as described herein.

Oligopeptide-68 is a TGF-β biomimetic peptide containing 12 amino acids (arginine, aspartic acid, glycine, glutamine, isoleucine, leucine, serine, threonine, tryptophan and tyrosine). A skin-brightening peptide claimed to have a unique mechanism of action on lightening both constitutive (the default skin color) and facultative (such as tanning) pigmentation. It works by inhibiting the MITF gene that plays an important role in controlling melanin producing skin cells called melanocytes. Oligopeptide-68 is commercially available in various forms, for example, as the product β-White™ wherein it is encapsulated in phospholipids liposome for better skin penetration and continuous release in the skin.

Niacinamide is a whitening assistant that inhibits the transfer of melanosomes from melanocytes to keratinocytes. Occurs as a component of a variety of biological systems, specifically the vitamin B3 complex.

Kojic acid is produced by several different types of fungi and is a byproduct of fermenting food. Kojic acid is often used topically to treat a number of different cosmetic conditions. It's been approved for use in cosmetic products in concentrations of ≤1%. It's most often used as a skin-lightening agent, because it prevents the formation of tyrosine, which is an amino acid that's needed to produce melanin. Products containing kojic acid are most commonly used on the face and hands but can be used on all non-sensitive areas of the body. Kojic's acid primary use and benefit is to lighten visible sun damage, age spots, or scars, resulting in an anti-aging effect on the skin. In addition to skin-lightening effects, kojic acid also contains some anti-microbial properties, and this can help treat acne. It may also lighten scars from acne that haven't faded yet.

The CIR Expert Panel decided that kojic acid is safe to use in cosmetics in concentrations of 1% w/w. However, some individuals may still experience side effects or risks from its use. Contact dermatitis is the most common side effect of kojic acid. It can manifest itself as redness, irritation, itchiness, rashes, swollen skin, or pain and discomfort. Contact dermatitis is most common in those with sensitive skin, or in individuals using a product with a higher concentration than 1% w/w of kojic acid.

Hydroquinone is a skin-lightening agent. It bleaches the skin, which can be helpful when treating different forms of hyperpigmentation. The bleach effect of hydroquinone is due to decreasing the number of melanocytes present in the skin. In cases of hyperpigmentation, more melanin is present due to an increase in melanocyte production. By controlling these melanocytes, the skin becomes more evenly toned over time. It takes about four weeks on average for the ingredient to take effect, and several months of consistent use before full results are seen. The FDA has confirmed that hydroquinone can be safely sold over the counter (OTC) in 2% w/w concentrations.

Formulations for treating pigmentation disclosed herein, also interchangeably referred to herein as "whitening formulations" or "lightening formulations", comprise a contemplated composition comprising a combination of MSM and strontium, and one or more melanin inhibitors such as:

(i) azelaic acid in an amount of form 0.1% w/w to 30% w/w, from example, form 0.1% w/w to 5% w/w, or from 10% to 30% w/w; (ii) hydroquinone in an amount of form 0.1% w/w to 10% w/w, for example, form 0.5% w/w to 3.0% w/w or form 1% w/w to 5% w/w; (iii) vitamin C or a derivative thereof in an amount of form 0.1% w/w to 40% w/w, for example, from 1% to 5% w/w, from 10% to 30% w/w, or from 5% to 10% w/w; (iv) alpha-arbutin or beta-arbutin in an amount of from 0.1% to 30% w/w, for example, from 1% to 20% w/w, from 1% to 5% w/w or from 5% to 10% w/w; or (v) kojic acid in an amount of from 0.1% to 10% w/w, for example, from 0.5% to 1.5% w/w, or from 1% to 5% w/w.

Some exemplary formulations comprise about 5% w/w alpha-arbutin, at least 10% w/w vitamin C, and/or vitamin C derivatives such as ascorbyl tetraisoplamitate (6% w/w) and ascorbyl glucoside (5% w/w), or at least 25% w/w azelaic acid. Contemplated formulations comprising 5% w/w alpha arbutin have proven to be skin lighteners that treat the brown-purple post-acne marks and prevent development of hyperpigmentation in healing lesions.

In some embodiments, a disclosed formulation is formulated as anti-aging formulations, thereby comprising a contemplated composition comprising a combination of MSM and strontium, and one or more anti-aging active agents such as, but not limited to, retinol, retinoic acid, vitamin A, peptides, Retin A, growth factors and ceramides.

Vitamin A is the first vitamin approved by the Food and Drug Administration as an anti-wrinkle agent that changes appearance of the skin surface and has anti-aging effects. Vitamin A is in a group of fat-soluble substances and belongs to the category of retinoids. Apart from retinol, that group includes structurally related substances with the biological properties of retinol such as retinoic aldehyde and retinoic acid (Retin-A). The term "retinoid", as used herein, refers to the synthetic and natural analogues of vitamin A. Vitamin A and its derivatives are among the most effective substances slowing the aging process. Retinoids regulate the cell apoptosis, differentiation and proliferation. Anti-wrinkle properties of retinoids promote keratinocytes proliferation, strengthen the protective function of the epidermis, restrain trans-epidermal water loss, protect collagen against degradation and inhibit metalloproteinases activity.

Retinol is one specific type of retinoid—the most common and proven retinoid sold over-the-counter. Dermatologists often refer to retinol as the "gold standard" anti-aging ingredient because it is widely available and has decades of research demonstrating its effectiveness in anti-aging treatment, stimulating collagen production, accelerating cell reproduction and normalizing skin keratinization. Retinol also provides effective antioxidant support and regeneration. It improves the skin elasticity, smoothness, softness, resulting in younger, clearer and healthier looking skin. For the treatment of acne, retinol is known to reduce sebum secretion from the sebaceous glands.

Retin-A is the brand name for the medication tretinoin, which is retinoic acid. Retin-A is a synthetic form of vitamin A i.e., an irreversibly oxidized form of retinol. Unlike retinols, Retin-A is a prescription-only medication. It's typically used to treat both inflammatory acne and comedonal breakouts. Retin-A's active ingredient, tretinoin, is also used to treat fine lines and wrinkles, brighten the complexion, and fade hyperpigmentation (dark marks left by acne breakouts or sun damage).

The safety of retinoids has been assessed by the CIR Expert Panel. The CIR Expert Panel concluded that this ingredient is safe as used in cosmetics at concentrations up to 5%. The use of retinol in cosmetic product is restricted in the Norwegian cosmetics regulations with maximum allowed concentrations of 0.3%.

Ceramides are lipids which are in natural concentration in the upper layers of the skin. They make up more than 50% of the composition of the skin and play a vital role in how the skin is structured and how it responds to the harmful effects of the environment. Synthetic ceramides are mostly used in skincare, they can be found in small amounts in different plants and animal tissues and are very expensive to produce.

Ceramides help maintain the structure of the skin by forming a protective layer on the surface of the skin. They limit the invisible water loss of the skin and prevent the entry of impurities and microorganisms. In addition, ceramides strongly contribute to the youthful and healthy appearance of the skin. They increase skin hydration and firmness.

Ceramides, particularly ceramide types 2, 3, 6, which find extensive use in cosmetic products as skim filling, constitute a perfect copy of the lipids found in the upper layer of the skin and thus help to rectify defects in the stratum corneum, forming a healthy layer resistant to damage.

Some exemplary anti-aging formulation contemplated herein comprise a retinoid, e.g., retinol or retinoic acid, in an amount of from about 0.1% to about 20% w/w, for example, from 0.1% to 1% w/w, from 0.5% to 2%, from 1% to 5% w/w, from 2% to 10% w/w or from 10% to 15% w/w.

In some embodiments, a disclosed formulation is formulated as a cleanser or soap. In accordance with these embodiments, a contemplate cleanser comprises a disclosed composition comprising strontium and MSM, and an active agent such as, but not limited to, myristic acid, sodium laureth sulfate, and disodium laureth sulfosuccinate.

CIR Expert Panel considers sodium laureth sulfate sate for use in cosmetics and personal care products when formulated to be non-irritating, and disodium laureth sulfosuccinate, safe when used in cosmetics at concentrations up to 10%, when formulated to be non-irritating.

Further active ingredients useful in cleansing formulations contemplated herein, such as deep cleansing foams and soaps, include ascorbyl tetraisopalmitate—an oil-soluble vitamin C derivative, and floral water of flowers of *Chamomilla recutita*, produced by distillation, e.g., medxtract Chamomile distilled. Medxtract Chamomile distilled is a gentle soothing hydrosol used to refresh and calm the skin.

Myristic Acid is a non-toxic fatty acid that occurs naturally in animal fats and most vegetables. Palm oil and Coconut oil contain relatively high values. It is used as a cleansing, surfactant and opacifying agent. The saturated fatty acid myristic acid has 14 carbon atoms and when saponified becomes sodium myristate. This product is not derived from any animal fats or oils. Myristic contributes hardness, cleansing, and fluffy lather.

Some exemplary cleansers contemplated herein comprise one or more of: myristic acid, sodium laureth sulfate, disodium laureth sulfosuccinate or medxtract chamomile distilled, each in an amount of from about 0.1% to about 50.0% w/w, for example, from 1.0% to 10.0% w/w, from 5.0% to 15.0%, from 10.0% to 5.0% w/w, or from 20.0% to 30.0% w/w, and any individual values or sub-ranges therebetween.

Trials demonstrated that when the combination of strontium and MSM is applied topically to the skin it immediately and effectively prevents the sensations of stinging, itching, burning, erythema and other sensations and feelings associated with skin irritant products and with change of temperatures and with burns and with change of pH and with chemical irritants among others, such as for example high concentration AHA or BHA peel or products containing retinols or alpha keto acids (such as pyruvic acid) or dicarboxylic acids (such as Azelaic Acid) or, for example, applying seawater to the skin after shaving.

Formulations containing the combination of strontium and MSM are effective in preventing the development and suppressing the irritation associated with products, which contain components capable of causing irritation.

In some embodiments, when a combination of strontium and methylsulfonylmethane is applied topically to the skin, it is immediately, effectively and for long period of time prevents the sensations of stinging, itching, burning, erythema and other sensations and feelings associated with skin irritant chemicals and products and other types of neurogenic inflammations.

The combination is also effective for treating sensations and neurogenic inflammation caused by chemicals, changes in temperature, burns among others, and from low pH, such as in AHA and BHA peel formulations, anti-aging formulation whitening formulation and the like, disclosed herein, comprising retinols and/or alpha keto acids, dicarboxylic acids (e.g., azelaic acid) and other types of chemical peels and other types of medical and cosmetics products that cause topical irritations. The combination of strontium and MSM significantly extends the duration of the anti-irritation effect compared to each one on its own. The anti-irritant effect is immediate and in real-time, with no need to wait between the time of applying the composition and the time it starts to have an effect.

In some embodiments the concentration of elemental strontium in a disclosed formulation is in a range of 0.1% to 10% w/w in the formulation. In some embodiments the concentration of strontium is in a range of 2-8% w/w in the formulation. In some embodiments the concentration of strontium is in a range of 2-4% w/ in the formulation. In some embodiments the concentration of strontium is in a range of 4-6% w/w in the formulation. In some embodiments the concentration of strontium is in a range of 6-8% w/w in the formulation. In some embodiments the concentration of strontium is in a range of 5-7% w/w in the formulation. In some embodiments the concentration of strontium is in a range of 2-5% w/w in the formulation. In some embodiments the concentration of strontium is in a range of 7-10% w/w in the formulation. In some embodiments the concentration of strontium is in a range of 8-10% w/w in the formulation. In some embodiments the concentration of strontium is in a range of 0.1-2% w/w in the formulation. In some embodiments the concentration of strontium is in a range of 0.1-15% w/w in the formulation. In some embodiments the concentration of strontium is in a range of 10-15% w/w in the formulation.

In some embodiments the concentration of strontium is in a range of 0.1 to 10% w/w in the formulation.

In some embodiments the concentration of strontium is in a range of 2-8% w/w in the formulation.

In some embodiments the concentration of MSM is in a range of 0.1 to 20% w/w in a disclosed formulation. In some embodiments the concentration of MSM is in a range of 5-10% w/w in the formulation. In some embodiments the concentration of MSM is in a range of 5-7% w/w in the formulation. In some embodiments the concentration of MSM is 7-10% w/w in the formulation. In some embodiments the concentration of MSM is in a range of 6-8% w/w in the formulation. In some embodiments the concentration of MSM is in a range of 6-9% w/w in the formulation. In some embodiments the concentration of MSM is in a range of 0.1-5% w/w in the formulation. In some embodiments the concentration of MSM is in a range of 10-20% w/w in the formulation. In some embodiments the concentration of MSM is in a range of 10-15% w/w in the formulation. In some embodiments the concentration of MSM is in a range of 15-20% w/w in the formulation. In some embodiments the concentration of MSM is in a range of 0.1-3% w/w in the formulation. In some embodiments the concentration of MSM is in a range of 3-5% w/w in the formulation. In some embodiments the concentration of MSM is in a range of 0.1 to 40% w/w in the formulation. In some embodiments the concentration of MSM is in a range of 20-40% w/w in the formulation. In some embodiments the concentration of MSM is in a range of 20-30% w/w in the formulation. In some embodiments the concentration of MSM is in a range of 30-40% w/w in the formulation.

In some embodiments the concentration of MSM is in a range of 0.1 to 20% w/w in the formulation.

In some embodiments the concentration of MSM is in a range of 5-10% w/w in the formulation.

The higher the concentration of the cosmetic active ingredient a higher concentration of the combination of stontium and MSM is recommended.

In some embodiments the counter anion for the strontium cation is a halogen.

In some embodiments the halogen is fluoride (F—), chloride (Cl—), bromide (Br—) or iodide (I—).

In some embodiments the halogen is chloride.

In some embodiments the counter anion is organic anion such as carboxylic acids, alkoxylates, amino acids (especially, lysine, arginine, histidine, ornithine, aspartic acid, glutamic acid, proline, and cysteine), peptides, saturated and unsaturated organic acids, and saturated and unsaturated fatty acids.

In some embodiments, the organic counter anion is acetate, lactate, glycolate, tartrate, maleate, benzoate, propionate, salicylate, ascorbate, formate, succinate, folinate, aspartate, phthalate, oleate, palmitate, stearate, lauryl sulfate, lanolate, myristate, behenate, caseinate, cyclamate, pantothenate, EDTA or other polyaminopolycarboxylates, saccharin, thioglycolate, laurate, methylparaben, propylparaben, ricinoleate or sorbate anions.

In some embodiments the strontium is in the form of strontium chloride, strontium acetate or strontium nitrate salt.

In some embodiments the strontium is in the form of strontium chloride hexahydrate.

In some embodiments a disclosed formulation further comprises a dermatologically acceptable carrier. A "dermatologically acceptable carrier" as used herein means a carrier suitable for topical application to keratinous tissue, and compatible with the actives in the formulation, that will not cause safety or toxicity concerns. Examples of dermatologically acceptable carriers are well known in the art and may comprise about 0.1 to 99.1% of a contemplated cosmetic formulation.

In some embodiments a disclosed composition is administered in any pharmaceutical or cosmetic formulation that enables the administration to a skin tissue of a patient.

In some embodiments a disclosed composition or a disclosed formulation comprising same, e.g., a topical medicament, comprises a carrier. According to some embodiments, the carrier is in the form of an ointment, a cream, a lotion, an oil, a solution (in some embodiments an aqueous solution), an emulsion, a gel, a paste, a milk, an aerosol, a powder, or a foam. In some embodiments the carrier is an aqueous-based carrier (such as a gel, oil-in water emulsion or oil-in water cream, aqueous solution, foam, lotion, spray). In some embodiments, the carrier is alcohol, e.g., ethanol.

In some embodiments, the composition comprising a combination of strontium and MSM as described herein is administered in products such as, but not limited to, a mask, a peel, a soap (liquid or solid), a shampoo, a shaving cream, after shave, sunscreen, perfume, deodorant, anti-aging and anti-wrinkle, artificial tanning, makeup and makeup removers, or baby products.

In some embodiments a disclosed formulation is in the form of a topical oral formulation. In some embodiments the formulation is administered in products such as mouthwash or lozenges. A physiologically acceptable carrier for topical administration as used herein includes the dermatologically acceptable carriers defined above, and carriers adapted for topical administration in the mouth.

Typical modes of application of a disclosed composition or formulation/product include fingers, a physical applicator such as a brush, as stick, swab, tissue or cloth, or by applying or adhering a prepared applicator already containing the formulation such as a cloth mask.

Any of the formulations disclosed herein, including the exemplary formulation described in Examples III-VII herein, comprise in addition to the relevant active agents and combination of MSM and strontium, further excipients, carriers and additives as well-known to a person skilled in the art of cosmetic products. Such excipients include, for example, emulsifiers, solvents, surfactants, preservatives, moisturizer, fragrances, dyes/colorants, viscosity adjustment agents, emollients, binders, absorbents, buffering agents, chelating agents, conditioning agents, in various concentrations ranging from 0.01% to 70% w/w.

The formulations disclosed herein all preserve the primary activity of the topical product while allowing the anti-irritation and anti-erythema activity of the formulation to provide patient benefit.

EXAMPLES

Example I—Glycolic Acid 50% (pH 0.9)

A cosmetic peel comprising Glycolic Acid 50% (pH 0.9) was administered to 15 volunteers, between the ages 23 to 64 years (Average 45). The peel was kept on the treated area for 10 minutes. Erythema and irritation (itching, stinging and burning) were evaluated before applying the product and 10 minutes after applying the product.

The peel further comprised one of the following combinations of Strontium Chloride and MSM:
No addition of Strontium Chloride and no addition of MSM;
10% MSM only;
5% Strontium Chloride only (which equals about 2.75% of elemental Strontium); or 5% Strontium Chloride+ 10% MSM.

Different types of skin tone (Fitzpatrick) and conditions (oily, regular, etc.) participated in the trials.

Erythema was evaluated using a colorimeter device that provides values using CIE-L*a*b* Coordinates.

Irritation was evaluated using standardized Visual Analogue Scale (VAS) of 0 to 10.

The results are presented below in table 1, wherein Delta a* is the difference in redness between the measurement before the peel and 10 minutes after the peel and Delta E* is difference in overall skin tone between the measurement before the peel and 10 minutes after the peel.

The first row in the table is the "base" row wherein the cosmetic peel was administered without Strontium and/or MSM. The last three columns in the table compare the change in Delta a*, Delta E* and irritation compared to the base line. For example, for the second row where 10% MSM was administered the Delta a* is 5.62 (an average for the participating subjects) which is 6.53% lower than the Delta a* of the base row as noted in column 4.

TABLE 1

| Formula | Delta a* | Delta E* | Irritation | Delta a* % from base | Delta E* % from base | Delta Irritation % from base |
|---|---|---|---|---|---|---|
| 0% Str. 0% MSM | 6.02 | 8.87 | 8.07 | | | |
| 0% Str. 10% MSM | 5.62 | 8.36 | 7.73 | −6.53% | −5.73% | −4.13% |
| 5% Str. 0% MSM | 5.44 | 7.99 | 6.93 | −9.57% | −9.95% | −14.05% |
| 5% Str. 10% MSM | 3.47 | 5.21 | 3.53 | −42.33% | −41.27% | −56.2% |

The synergistic effect of the combination can be clearly seen form the results in Table 1. The Delta a* of 10% MSM on its own is 5.62 and the reduction compared to the base is 6.53%, the Delta a* of 5% Strontium Chloride on its own is 5.44 and the reduction compared to the base is 9.57%, while the Delta a* of the combination of 10% MSM and 5% Strontium Chloride is 3.47 which is a 42.33% reduction compared to the base. This reduction is more than the sum of each of the reductions on their own and accordingly demonstrates the synergistic effect.

The effect of the combination is also illustrated in the figures and described below.

FIG. 1 depicts comparative clinical data from Example 1 showing an effect on skin redness (delta a*) with formulations according to the disclosure. Delta a*% represents the percent of increase in redness of the skin after applying the peel compared to the color before. The graph indicates this change for each of the 15 volunteers. As can be seen, the top three graph lines, which include the following three combination: no addition of Strontium Chloride and no addition of MSM; 10% MSM only and 5% Strontium Chloride only, show an increase of about 30-35% in redness while the combination of 5% Strontium Chloride and 10% MSM shows in increase on average of only about 20%.

Figure 2:
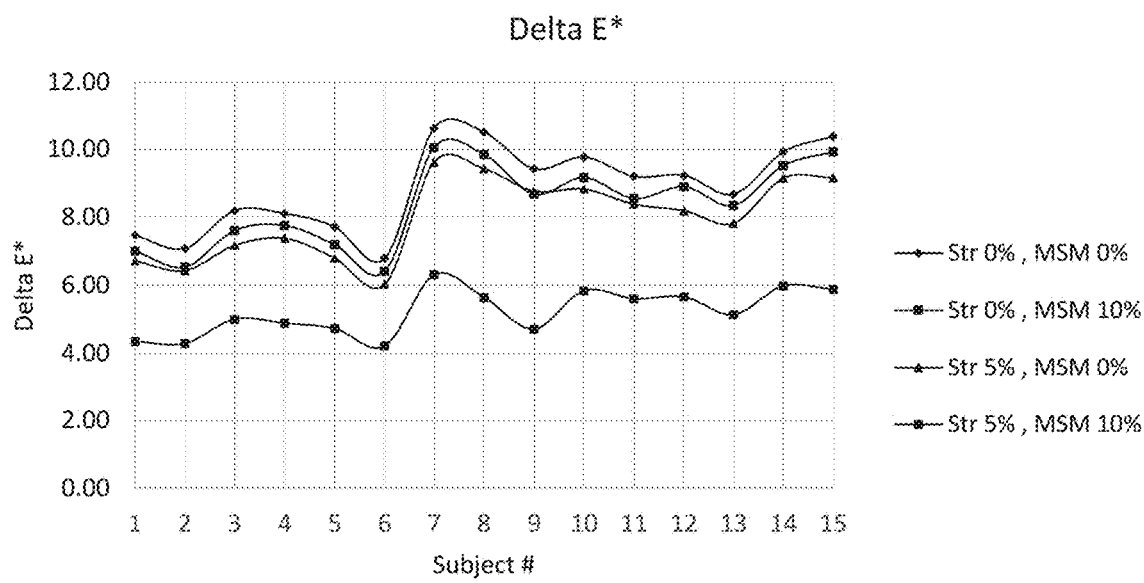
FIG. 2 depicts comparative clinical data from Example 1 showing an effect on overall skin color (delta E*) with formulations according to the disclosure.

FIG. 2 depicts comparative clinical data from Example 1, showing an effect on overall skin color (delta E*) with formulations according to the disclosure. Delta E* represents the difference in overall skin tone between the measurement before the peel and after the peel. The graph indicates this change for each of the 15 volunteers. As can be seen, the overall skin tone change for the combination of 5% Strontium Chloride and 10% MSM was lower than the other three combinations.

Figure 3:
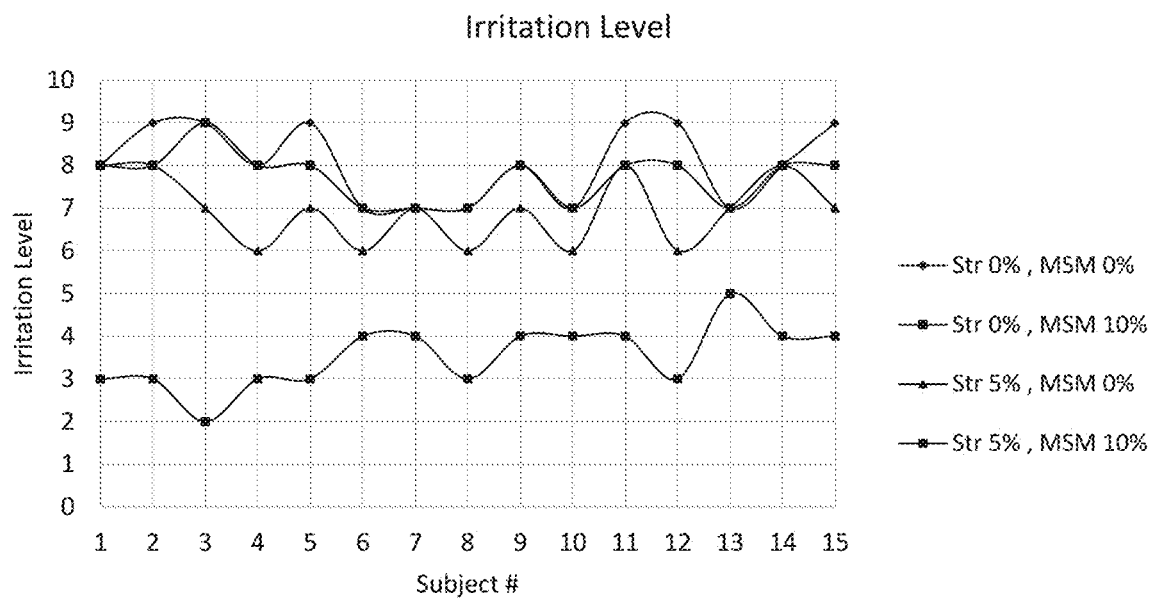
FIG. 3 depicts comparative clinical data from Example 1 showing an effect on skin irritation level with formulations according to the disclosure.

FIG. 3 depicts comparative clinical data from Example 1, showing an effect on skin irritation level with formulations according to the disclosure. The graph indicates the irritation level for each of the 15 volunteers, measured 10 minutes after applying the peel. As can be seen the irritation level for the combination of 5% Strontium Chloride and 10% MSM was lower than the level for the other three combinations.

Figure 4:
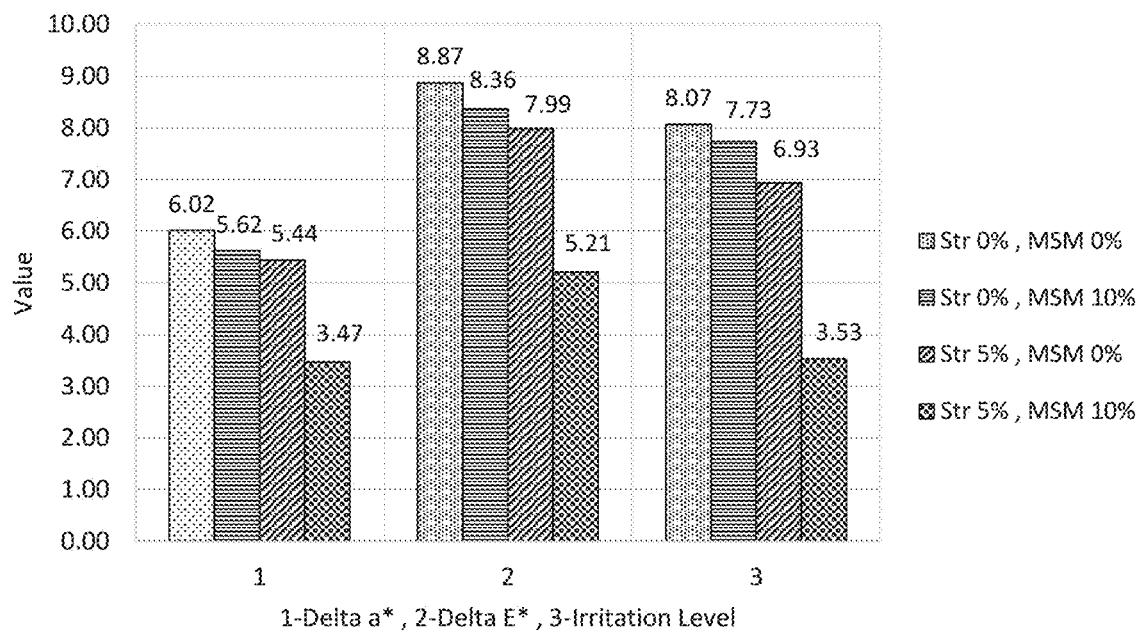
FIG. 4 depicts a comparison of the data shown in table 1.

FIG. 4 depicts a comparison of the data shown in Table 1, columns 1-3, and demonstrating the lower values, in all three parameters of Delta a*, Delta E* and irritation, of the combination of 5% Strontium Chloride and 10% compared to the other three combinations.

Figure 5:
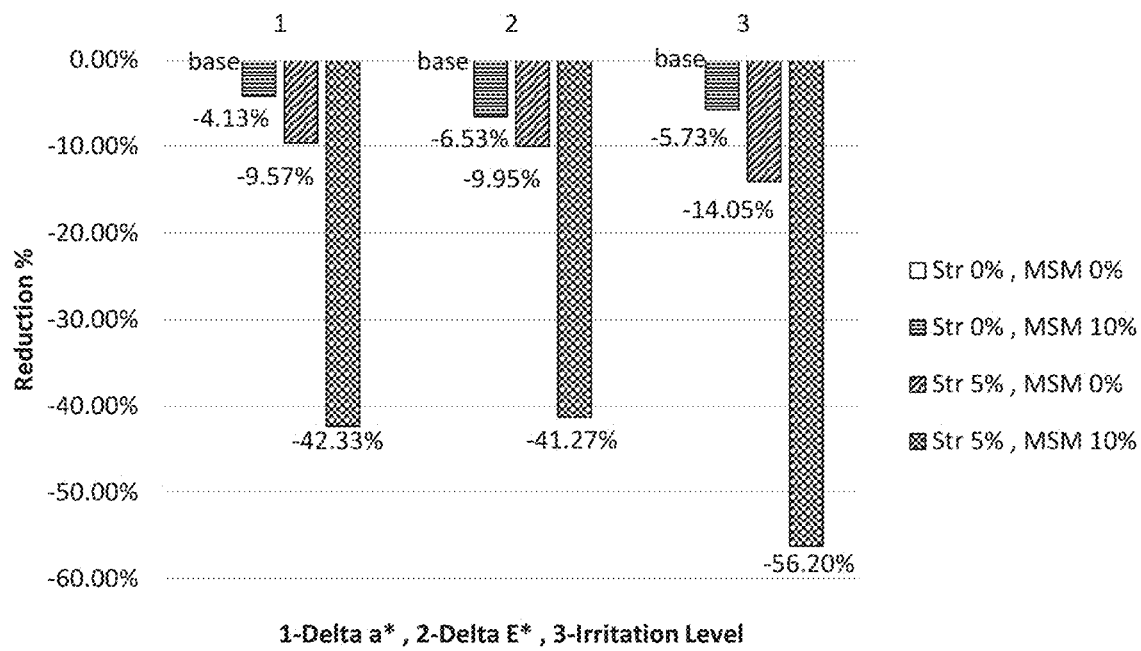
FIG. 5 depicts a comparison of improvement-from-baseline of the data shown in table 1.

FIG. 5 depicts a comparison of improvement-from-baseline (no addition of Strontium Chloride and no addition of MSM) of the data shown in Table 1, columns 4-6, and demonstrating the higher reduction percentages compared to the base line, in all three parameters of Delta a*, Delta E* and irritation, of the combination of 5% Strontium Chloride and 10% compared to the other two combinations.

Example II—Azelaic Acid 25% (pH 3.5)

A cosmetic product comprising Azelaic Acid 25% (pH 3.5) was administered to 15 volunteers, between the ages 23 to 64 years (Average 45). Erythema and irritation (itching, stinging and burning) were evaluated before applying the product and 10 minutes after applying the product.

The product further comprised one of the following combinations of Strontium Chloride and MSM:
No addition of Strontium Chloride and no addition of MSM;
10% MSM only;
5% Strontium Chloride only (which equals about 2.75% of elemental Strontium); or
5% Strontium Chloride+10% MSM.

Different types of skin tone (Fitzpatrick) and condition (oily, regular etc.) participated in the trials.

Erythema was evaluated using a colorimeter device that provides values using CIE-L*a*b* Coordinates.

Irritation was evaluated using standardized Visual Analogue Scale (VAS) of 0 to 10.

The results are presented below in table 2, wherein Delta a* is the difference in redness between the measurement before applying the product and 10 minutes after the applying the product and Delta E* is difference in overall skin tone between the measurement before applying the product and 10 minutes after applying the product.

The first row in the table is the "base" row wherein the cosmetic product was administered without Strontium and/or MSM. The last three columns in the table compare the change in Delta a*, Delta E* and irritation compared to the base line. For example, for the second row where 10% MSM was administered the Delta a* is 4.35 which is 3.77% lower than the Delta a* of the base row, as noted in column 4.

TABLE 2

| Formula | Delta a* | Delta E* | Irritation | Delta a* % from base | Delta E* % from base | Delta Irritation % from base |
|---|---|---|---|---|---|---|
| 0% Str. 0% MSM | 4.52 | 6.35 | 5.6 | | | |
| 0% Str. 10% MSM | 4.35 | 6.08 | 4.87 | −3.77% | −4.27% | −13.10% |
| 5% Str. 0% MSM | 4.12 | 5.73 | 4.73 | −8.83% | −9.72% | −15.48% |
| 5% Str. 10% MSM | 2.6 | 3.71 | 2.4 | −42.47% | −41.57% | −57.14% |

The synergistic effect of the combination can be clearly seen form the results in Table 2. The Delta a* of 10% MSM on its own is 4.35 and the reduction compared to the base is 3.77%, the Delta a* of 5% Strontium on its own is 4.12 and the reduction compared to the base is 8.83%, while the Delta a* of the combination of 10% MSM and 5% Strontium is 2.6 which is a 42.47% reduction compared to the base. This reduction is more than the sum of each of the reductions on their own and accordingly demonstrates the synergistic effect.

The effect of the combination is also illustrated in the figures.

Figure 6:
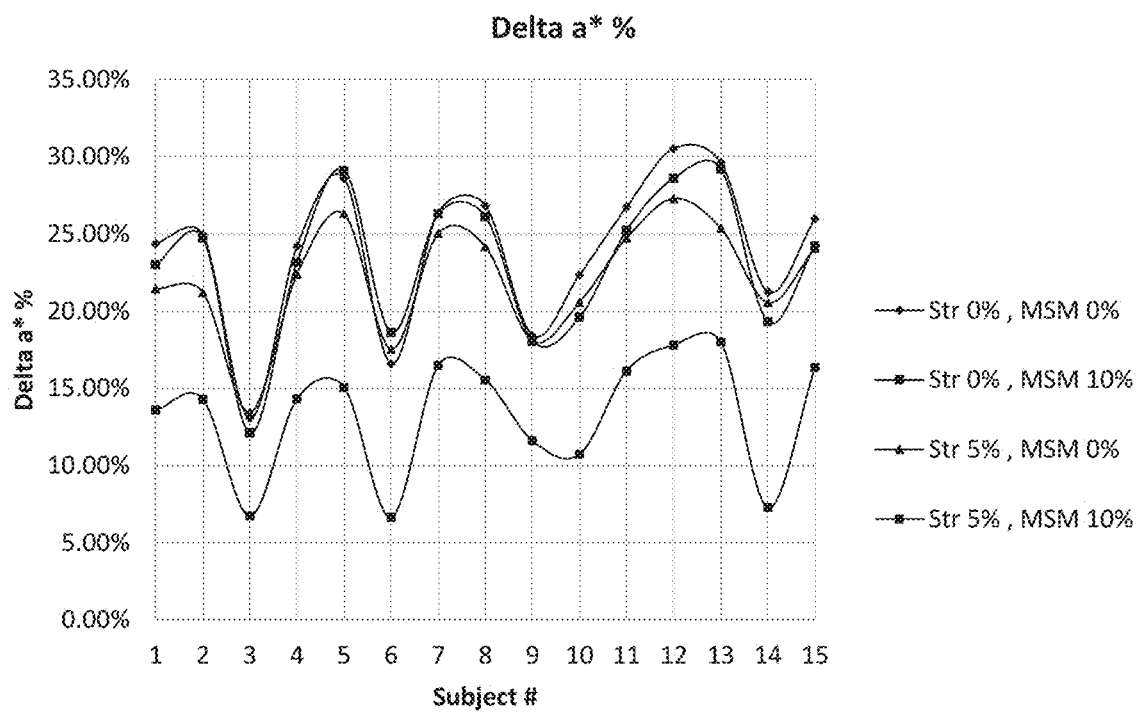
FIG. 6 depicts comparative clinical data from Example II showing an effect on skin redness (delta a*) with formulations according to the disclosure.

FIG. 6 depicts comparative clinical data from Example II showing an effect on skin redness (delta a*) with formulations according to the disclosure. Delta a*% represents the percent of increase in redness of the skin after applying the product compared to the color before. The graph indicates this change for each of the 15 volunteers. As can be seen, the top three graph lines, which include the following three combination: no addition of Strontium Chloride and no addition of MSM; 10% MSM only and 5% Strontium Chloride only, show an increase of about 20-25% in redness while the combination of 5% Strontium Chloride and 10% MSM shows in increase on average of only about 10-15%.

Figure 7:
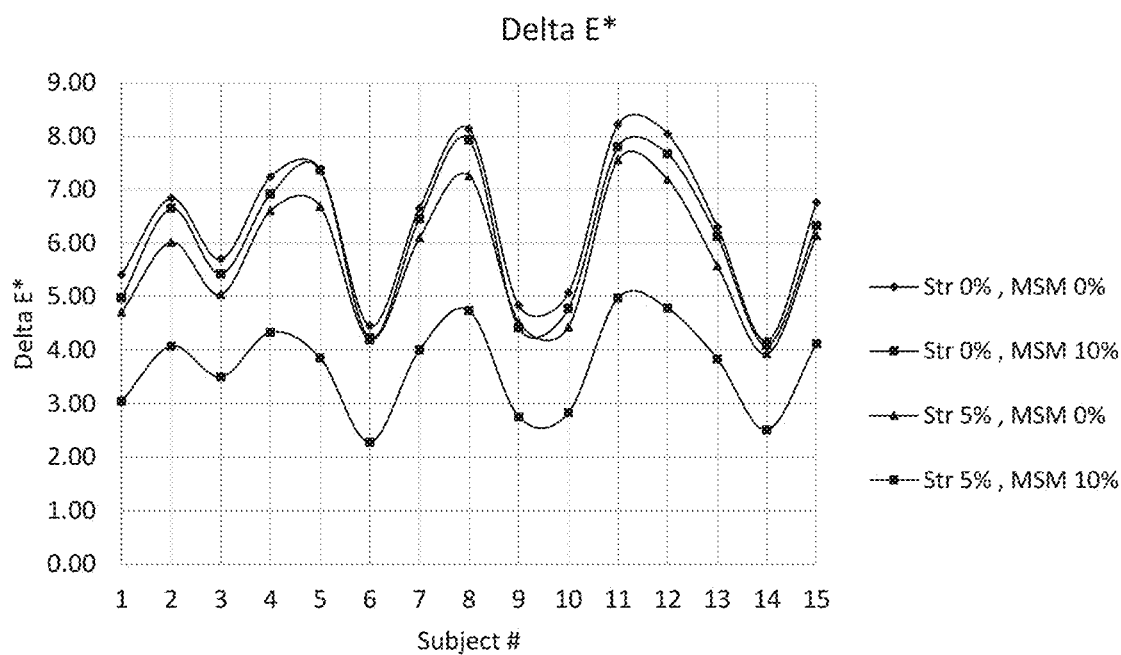
FIG. 7 depicts comparative clinical data from Example II showing an effect on overall skin color (delta E*) with formulations according to the disclosure.

FIG. 7 depicts comparative clinical data from Example II showing an effect on overall skin color (delta E*) with formulations according to the disclosure. Delta E* represents the difference in overall skin tone between the measurement before the product and after the product. The graph indicates this change for each of the 15 volunteers. As can be seen, the overall skin tone change for the combination of 5% Strontium Chloride and 10% MSM was lower than the other three combinations.

Figure 8:
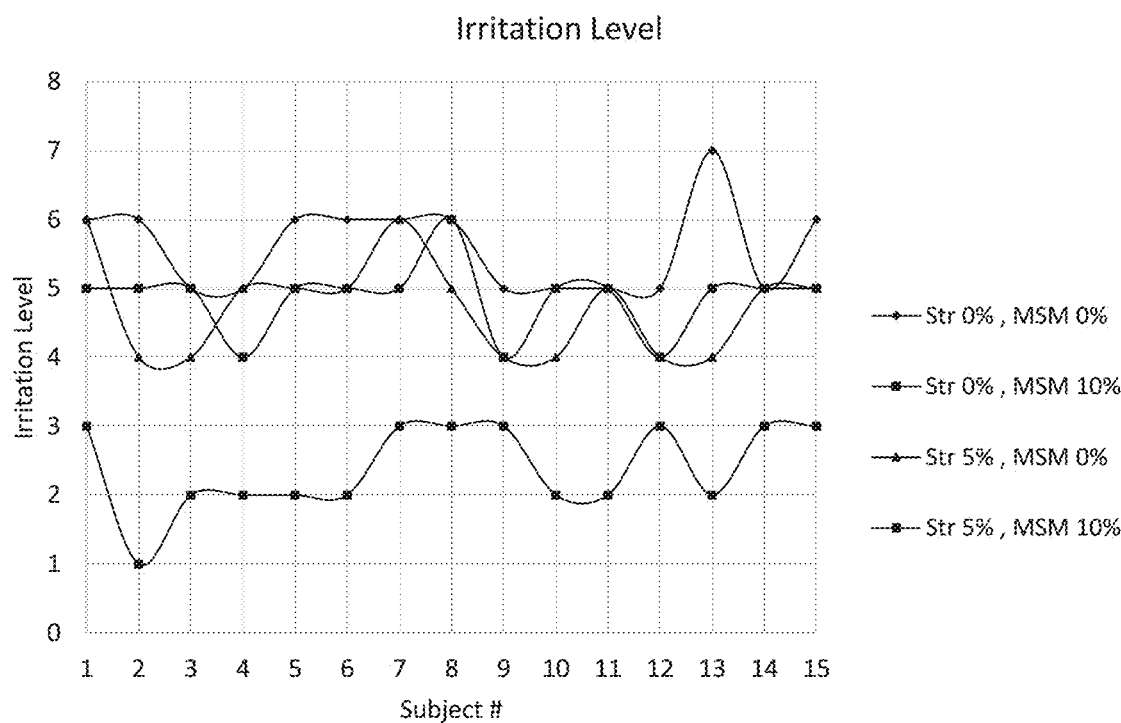
FIG. 8 depicts comparative clinical data from Example II showing an effect on skin irritation level with formulations according to the disclosure.

FIG. 8 depicts comparative clinical data from Example II showing an effect on skin irritation level with formulations according to the disclosure. The graph indicates the irritation level for each of the 15 volunteers, measured 10 minutes after applying the product. As can be seen the irritation level for the combination of 5% Strontium Chloride and 10% MSM was lower than the level for the other three combinations.

Figure 9:
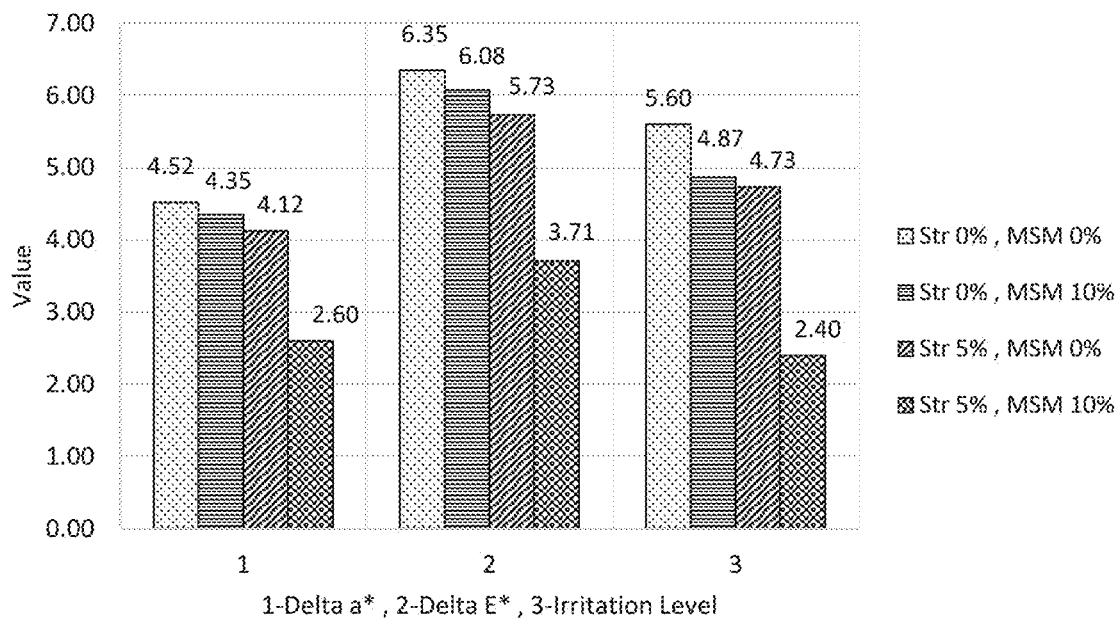
FIG. 9 depicts a comparison of the data shown in table 2.

FIG. 9 depicts a comparison of the data shown in Table 2, columns 1-3, and demonstrating the lower values, in all three parameters of Delta a*, Delta E* and irritation, of the combination of 5% Strontium Chloride and 10% compared to the other three combinations.

Figure 10:
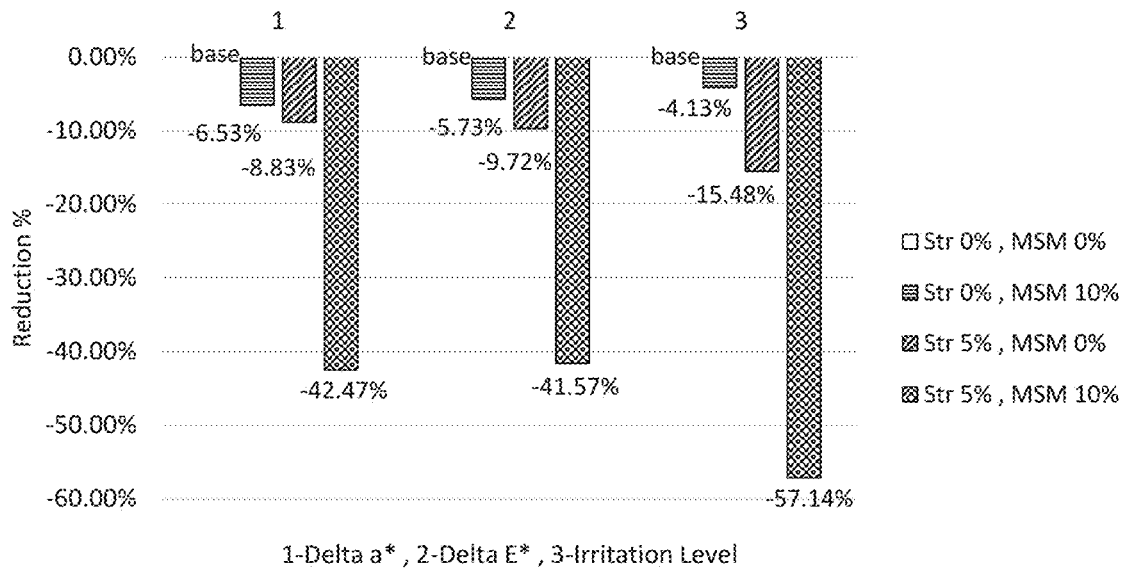
FIG. 10 depicts a comparison of improvement-from-baseline of the data shown in table 2.

FIG. 10 depicts a comparison of improvement-from-baseline (no addition of Strontium Chloride and no addition of MSM) of the data shown in Table 2, columns 4-6, and demonstrating the higher reduction percentages compared to the base line, in all three parameters of Delta a*, Delta E* and irritation, of the combination of 5% Strontium Chloride and 10% compared to the other two combinations.

Example III—Formulations for Skin Peeling and Rejuvenation

Concentrations of ingredients are provided throughout this specification in units of weight percent, also denoted herein, interchangeably, as "Wt %", "weight %", or "w/w", meaning, certain grams of an ingredient in 100 grams of the final product.

(i) Face Cream for Skin Peeling Comprising Lactic Acid

A cream useful for intensive rejuvenating and hydrating, comprising lactic acid in an amount of 11.36 Wt % was prepared using the ingredients listed in Table 3. This formulation is referred to herein as "Lacto-10". Some physical and chemical characteristics of Lacto-10 are presented in Table 4.

TABLE 3

Face peeling cream Lacto-10

| Ingredient | Concentration in final product [weigh %] | Main Functions |
| --- | --- | --- |
| Lactic acid cosmetic grade 88% | 11.36 | Skin peeling |
| Dermofeel ® PA-3 (sodium phytate + alcohol and water) | 0.10 | Chelating agent |
| MSM | 5.00 | Calming, soothing, masking |
| Strontium Chloride | 5.00 | Calming, soothing, masking |
| Propanediol | 4.00 | Viscosity controlling |
| Xanthan Gum | 0.20 | Binding, emulsion stabilizing, viscosity controlling |
| Verstatil ® PC (phenoxyethanol + caprylyl glycol) | 1.00 | Preservative, emollient |
| Sodium hydroxide | 2.60 | Buffering, denaturant |
| BC2335 (cyclopentasiloxane + dimethicone) | 4.00 | Skm conditioning, antifoaming, emollient |
| Isopropyl myristate | 5.00 | Binding, emollient, masking, |
| Octyl Palmitate | 5.00 | Emollient, perfuming |
| Alcohol cetyl | 1.50 | Emollient, emulsifying, emulsion stabilizing, viscosity controlling |
| Sabowax ™ FL 65/k (glyceryl stearate + PEG-100 stearate) | 2.00 | Surfactant |
| Steareth-2 | 1.50 | Emulsifying, Surfactant |
| PEG-150 distearate | 1.50 | Emulsifying, surfactant |
| Parfum | 0.20 | Perfuming |
| Limon Oil | 0.34 | Masking, perfuming, allergen |
| Water | 49.84 | Solvent |

TABLE 4

Physical/chemical characteristics of face cream Lacto-10

| Test | Specification | Units | Method |
| --- | --- | --- | --- |
| Appearance | Gel cream | — | Visual check |
| Odor | None | — | Organoleptic test |
| Color | Whitish to yellowish | — | Visual test |
| Density | 0.975-1.100 | g/ml | QC-F-03 |
| pH (at 25° C.) | 3.0-4.5 | — | QC-F-03 |

This face cream, when applied, for example, around the eyes and on the neck, has been shown to hasten skin rejuvenation, refine skin texture, improve hue and moisture (NMF), without having photosensitivity. It also harmonized nicely with other cosmetic preparations or medical ointments.

(ii) Liquid Formulation for Skin Peeling Comprising Glycolic Acid

A skin exfoliating solution useful in skin peeling of, e.g., face and neck, comprising glycolic acid in an amount as high as 34.5% w/w and a combination of MSM and strontium chloride was prepared using the ingredients listed in Table 5. This formulation is referred to herein as "G Peel 50".

Preliminary tests in rabbits demonstrated mild skin irritant effect of glycolic acid applied alone at 10% w/w, and moderate skin irritant at 30% or 40% w/w. However, a concentration of glycolic acid as high as of 34.5% w/w in a liquid formulation disclosed herein further comprising MSM and strontium chloride, caused only mild irritation. Some physical and chemical characteristics of G Peel 50 are presented in Table 6.

TABLE 5

Skin exfoliating formulation G Peel 50

| Ingredient | Concentration in final product [weigh %] | Main Functions |
| --- | --- | --- |
| Glycolic acid | 34.5 | Skin peeling |
| MSM | 5.0 | Calming, soothing, masking |
| Strontium Chloride | 10.0 | Calming, soothing, masking |
| Natrosol ™ 250 HR/HHR (hydroxyethylcellulose + sodium sulfate) | 0.5 | Bulking, emulsion stabilizing, viscosity controlling |
| Water | 50.0 | Solvent |

TABLE 6

Physical/chemical characteristics of G Peel 50

| Test | Specification |
| --- | --- |
| Appearance | Liquid |
| Odor | Characteristic |
| Color | Colorless |
| Density | 1.27-1.29 g/ml |
| pH (at 25° C.) | 3.36-0.39 |

This formulation has been shown to affect the epidermis by exfoliation and by stimulating basal layer corneocytes turnover. It affects the dermis by stimulating dermal fibroblasts to create collagen, elastin and glycosaminoglycan synthesis. The formulation has been shown to significantly improve skin texture, reduce fine lines, wrinkles, sun damage and hyper-pigmentation.

(iii) Alcoholic Liquid Formulation for Skin Peeling Comprising Salicylic Acid

An alcohol-based skin exfoliant solution useful in skin peeling comprising salicylic acid was prepared using an extract of the leaves of the wintergreen plant, *Gaultheria procumbens L*, Ericaceae, serving as a natural source for salicylic acid 2% w/w.

Further ingredients in the alcohol-based formulation, herein referred to as "S Peel 20", are listed in Table 7. Some physical and chemical characteristics of S Peel 20 are presented in Table 8.

TABLE 7

Skin exfoliating formulation S Peel 20

| Ingredient | Concentration in final product [weigh %] | Main Functions |
| --- | --- | --- |
| *Gaultheria procumbens* leaf extract (containing salicylic acid as the peeling active ingredient) | 20.0 | Skin peeling |
| MSM | 5.0 | Calming, soothing, masking |
| Strontium Chloride | 5.0 | Calming, soothing, masking |
| Ethanol | 65.0 | Solvent |
| Water | 5.0 | Solvent |

TABLE 8

Physical/chemical characteristics of S Peel 20

| Test | Specification |
| --- | --- |
| Appearance | Liquid |
| Odor | Characteristic |
| Color | Colorless |
| Density | 0.85-0.87 g/ml |
| pH (at 25° C.) | 2.0-2.5 |

This formulation has been shown to significantly improve skin texture, reduce fine lines, wrinkles, sun damage and hyper-pigmentation. Due to the anti-inflammatory properties of salicylic acid, the formulation has been shown to be effective in treating acne as well.

(iv) Alcoholic Formulation for Skin Peeling Comprising Salicylic Acid and Lactic Acid A skin exfoliating solution useful in skin peeling and rejuvenation comprising both the AHA lactic acid and the BHA salicylic acid was prepared using an extract of the leaves of the wintergreen plant, *Gaultheria procumbens L.*, Ericaceae, serving as a natural source for salicylic acid 2%. The total amount of acid in the formulation providing the peeling effect was 40% w/w, which is about 4 times the amount used in common peeling products.

Further ingredients in the alcohol-based formulation, herein referred to as "J Peel Delicate", are listed in Table 9. Some physical and chemical characteristics of J Peel Delicate are presented in Table 10.

TABLE 9

Skin exfoliating formulation J Peel Delicate

| Ingredient | Concentration in final product [weigh %] | Main Functions |
| --- | --- | --- |
| Lactic acid cosmetic grade 88% | 16.0 | Skin peeling |
| MSM | 5.0 | Calming, soothing, masking |
| Strontium Chloride | 5.0 | Calming, soothing, masking |
| Citric acid | 12.0 | Buffering, chelating masking |
| *Gaultheria procumbens* leaf extract (containing salicylic acid | 14 | Skin peeling |
| Ethanol | 43 | Solvent |
| Water | 5.0 | Solvent |

TABLE 10

Physical/chemical characteristics of J Peel Delicate

| Test | Specification |
| --- | --- |
| Appearance | Liquid |
| Odor | Characteristic |
| Color | Beige |
| Density | 0.75-0.80 g/ml |
| pH (at 25° C.) | 0.4-0.7 |
| Stability (84 days at 40° C.) | Good: no separation to phases, no aggregates, no change of color and odor. |

This cosmetic product did not require challenge testing due to its low pH value and high alcohol content. Since there is no growth of microorganisms, this product is considered as a low-risk product. The formulation can be used in combination with other peels and/or in any anti-aging or beauty treatment. It has been found effective for acne, both inflammatory or post-inflammatory, and excellent for seborrhea treatment.

Example IV—Formulations for Treating Acne (i) Face Cream

A face cream for treatment of acne, comprising azelaic acid as the main anti-acne active agent, was prepared using the ingredients listed in Table 11. This formulation is referred to herein as "Azelaic Acid 20". Some physical and chemical characteristics of Azelaic Acid 20 are presented in Table 12.

TABLE 11

Anti-acne face cream Azelaic Acid 20

| Ingredient | Concentration in final product [weigh %] | Main Functions |
|---|---|---|
| Azelaic acid | 20.00 | Anti-acne |
| Propanediol | 6.00 | Solvent, viscosity controlling |
| MSM | 5.00 | Calming, soothing, masking |
| Strontium Chloride | 5.00 | Calming, soothing, masking |
| Propylene glycol | 10.00 | Humectant, penetration enhancer |
| Dermofeel ® PA-3 (sodium phytate + alcohol and water) | 0.10 | Chelating agent |
| Glycerin | 3.00 | Humectant, masking |
| Sodium hydroxide | 1.00 | Buffering, denaturant |
| BC2335 (cyclopentasiloxane + dimethicone) | 4.00 | Skin conditioning, antifoaming, emollient |
| Montanov ™ 202 (behenyl alcohol + glucose) | 1.00 | Binding, viscosity controlling, surfactant |
| Sabowax ™ FL 65/k (glyceryl stearate + PEG-100 stearate) | 4.00 | Surfactant, emollient |
| Cetyl palmitate | 1.00 | Emollient, skin conditioning |
| Dimethyl isosorbide | 2.00 | solvent |
| Cetyl alcohol | 0.50 | Emollient, emulsion stabilizing, viscosity controlling |
| Isononyl isononanoate | 4.50 | Antistatic, emollient, skin conditioning |
| Verstatil ® PC (caprylyl glycol + phenoxyethanol | 1.00 | Skin conditioning |
| alpha-Arbutin | 5.00 | Antioxidant, skin conditioning |
| AQUAXYL ™ (xylitylglucoside + anhydroxylitol + xylitol) | 2.00 | Moisturizing, stimulating the skin's natural production of hyaluronic acid |
| Propolis hydroglycerin extract (waxy component of the resinous material found in beehives) | 1.00 | Skin protecting, antiviral antibacterial |
| Parfum (limonene) | 0.20 | Perfuming |
| Citrus Medical Limonum Peel Oil | 0.20 | Masking, perfuming, allergen |
| Water | 23.35 | Solvent |

TABLE 12

Physical/chemical characteristics of face cream Azelaic Acid 20

| Test | Specification | Units | Method |
|---|---|---|---|
| Appearance | White cream | — | Visual check |
| Odor | Citrus | — | Organoleptic test |
| Color | White | — | Visual test |
| pH (at 25° C.) | 3.4-4.4 | — | QC-F-03 |

(ii) Therapeutic Hydrogel

An intensive hydrogel for treatment of acne, comprising lactic acid as the main anti-acne active agent, was prepared using the ingredients listed in Table 13. Some physical and chemical characteristics of the hydrogel are presented in Table 14.

TABLE 13

Anti-acne therapeutic hydrogel

| Ingredient | Concentration in final product [weigh %] | Main Functions |
|---|---|---|
| Lactic acid cosmetic grade 88% | 11.36 | Anti-acne |
| *Gaultheria procumbens* leaf extract (source for 2% salicylic acid) | 2.00 | Anti-acne |
| Propanediol | 6.00 | Solvent, viscosity controlling |
| MSM | 5.00 | Calming, soothing, masking |
| Strontium Chloride | 5.00 | Calming, soothing, masking |

TABLE 13-continued

Anti-acne therapeutic hydrogel

| Ingredient | Concentration in final product [weigh %] | Main Functions |
|---|---|---|
| Tween 20 | 1.00 | surfactant |
| Dermofeel ® PA-3 (sodium phytate + alcohol and water) | 0.10 | Chelating agent |
| BC2335 (cyclopentasiloxane + dimethicone) | 4.00 | Skin conditioning, antifoaming, emollient |
| Sodium hydroxide | 2.60 | Buffering, denaturant |
| SepiMax ™ ZEN (Polyacrylate cross polymer-6 + t-butyl alcohol) | 1.30 | Thickening, stabilizing and texturizing |
| Xyliance (Cetearyl wheat straw glycosides (and) cetearyl alcohol. | 1.30 | Hot process emulsifier, surfactant, solubilizer |
| Sabowax ™ FL 65/k (glyceryl stearate + PEG-100 stearate) | 1.40 | Emulsifying O/W base |
| Ethylhexyl stearate | 1.00 | Emollient |
| Cetyl alcohol | 0.70 | Emollient, emulsion stabilizing, viscosity controlling |
| Isononyl isononanoate | 1.00 | Antistatic, emollient, skin conditioning |
| Verstatil ® PC (caprylyl glycol + phenoxyethanol | 1.0 | Skin conditioning |
| Parfum (limonene) | 0.55 | Perfuming |
| Citronellyl methylcrotonate | 1.00 | Masking, perfuming |
| Water | 53.84 | Solvent |

TABLE 14

Physical/chemical characteristics of the therapeutic hydrogel

| Test | Specification | Units | Method |
|---|---|---|---|
| Appearance | Gel cream | — | Visual check |
| Odor | None | — | Organoleptic test |
| Color | Whitish to yellowish | — | Visual test |
| Density | 0.975-1.100 | g/ml | QC-F-03 |
| pH (at 25° C.) | 3.0-4.5 | — | QC-F-03 |

The intensive hydrogel has been shown to improve the quality of oily/combination skin, promote cell exfoliation, renew the epidermis, remove greasy appearance. It provided an intensive treatment without causing irritations.

(iii) Face Cream

A face cream for treatment of acne, comprising 25% w/w azelaic acid and 5% w/w alpha-arbutin as the main anti-acne active agents, was prepared using the ingredients listed in Table 15. This formulation is referred to herein as "Azelaic Forte 25". Some physical and chemical characteristics of Azelaic Forte 25 are presented in Table 16.

TABLE 15

Anti-acne face cream Azelaic Forte 25

| Ingredient | Concentration in final product [weigh %] | Main Functions |
|---|---|---|
| Azelaic acid | 25.00 | Anti-acne |
| Propanediol | 6.00 | Solvent, viscosity controlling |
| MSM | 5.00 | Calming, soothing, masking |
| Strontium Chloride | 5.00 | Calming, soothing, masking |
| Propylene glycol | 10.00 | Humectant, penetration enhancer |
| Dermofeel ® PA-3 (sodium phytate + alcohol and water) | 0.10 | Chelating agent |
| Glycerin | 3.00 | Humectant, masking |
| Sodium hydroxide | 1.00 | Buffering, denaturant |
| BC2335 (cyclopentasiloxane + dimethicone) | 4.00 | Skin conditioning, antifoaming, emollient |
| Montanov ™202 (behenyl alcohol + glucose) | 1.00 | Binding, viscosity controlling, surfactant |
| Sabowax ™ FL 65/k (glyceryl stearate + PEG-100 stearate) | 4.00 | Surfactant, emollient |
| Cetyl palmitate | 1.00 | Emollient, skin conditioning |
| Dimethyl isosorbide | 2.00 | solvent |
| Cetyl alcohol | 0.50 | Emollient, emulsion stabilizing, viscosity controlling |

TABLE 15-continued

Anti-acne face cream Azelaic Forte 25

| Ingredient | Concentration in final product [weigh %] | Main Functions |
|---|---|---|
| Isononyl isononanoate | 4.50 | Antistatic, emollient, skin conditioning |
| Verstatil ® PC (caprylyl glycol + phenoxyethanol | 1.00 | Skin conditioning |
| alpha-Arbutin | 5.00 | Antioxidant, skin Conditioning, anti acne |
| AQUAXYL ™ (xylitylglucoside + anhydroxylitol + xylitol) | 2.00 | Moisturizing, stimulating the skin's natural production of hyaluronic acid |
| Propolis hydroglycerin extract (waxy component of the resinous material found in beehives) | 1.00 | Skin protecting, antiviral antibacterial |
| Parfum (limonene) | 0.20 | Perfuming |
| Citrus Medica Limonum Peel Oil | 0.20 | Masking, perfuming, allergen |
| Water | 18.00 | Solvent |

TABLE 16

Physical/chemical characteristics of face cream Azelaic Forte 25

| Test | Specification | Units | Method |
|---|---|---|---|
| Appearance | Gel cream | — | Visual check |
| Odor | Citrus | — | Organoleptic test |
| Color | Whitish | — | Visual test |
| Density | 0-975-1.100 | g/ml | QC-F-03 |
| pH (at 25° C.) | 3.0-5.0 | — | QC-F-03 |

This formulation for treatment of acne, combining 25% azelaic acid and 5% alpha-arbutin has been shown to improve the quality of problematic skin, reduce excess of bacteria, ameliorate pigmentation (post-acne, solar, melasma), effective in treating powerful rosacea (bumps, lesions and swelling), improve the quality of skin damaged by sun exposure, even-out the skin tone. It is, therefore, suitable for all skin types and Fitzpatrick.

Example V—Formulations for Treating Pigmentation (Whitening Formulations)

An exemplary formulation for whitening treatment, is Azelaic Forte 25 described in Example IV above. This formulation used as a skin lightener is considered safe and uniquely suitable for treating darker skin types on a year-round regime since it does not cause skin photo-sensitivity, and since it selectively whitens only hyper-pigmentation spots without affecting normally pigmented skin. It has been shown to treat and prevent post-inflammatory hyper-pigmentation that usually appears on acne lesions in patients with skin photo types IV-VI (Fitzpatrick classification for dark skin). The added combination of MSM and strontium salt allows to use this extremely high and unique concentration of azelaic acid, (25% w/w) without the usual irritation.

Example VI—Anti-aging Formulations

Formulations disclosed herein, for treating aging manifestations in the skin, also referred to herein as "anti-aging formulations", comprise a contemplated composition comprising a combination of MSM and strontium, and one or more anti-aging active agents such as, but not limited to, retinol, retinoic acid, vitamin A, peptides, Retin A, growth factors and ceramides.

Anti-Aging Face Creams

Anti-aging face creams, comprising retinol as the main anti-aging active agent, were prepared using 3 different concentrations of retinol: 0.3%, 1.0% and 1.6% w/w. The ingredients for preparation of these products, herein also designated as "Retinol Charisma Delicate Instant Lift Retinol, 0.3%", "Retinol Charisma Delicate Instant Lift Retinol, 1.0%", and "Retinol Charisma Delicate Instant Lift Retinol, 1.6%", are listed in Table 17 (the amounts of retinol in the 0.3%, 1.0% and 1.6% formulations are 0.26%, 1.54% and 2.74% w/w, respectively). Some physical and chemical characteristics of Retinol Charisma Delicate Instant Lift Retinol, 0.3% are presented in Table 18.

TABLE 17

Anti-aging face creams Retinol Charisma Delicate Instant Lift Retinol, 0.3%/1.0%/1.6%

| Ingredient | Concentration in final product [weigh %] | Main Functions |
|---|---|---|
| Retinol | 0.26/1.54/2.74 | Anti-aging |
| Tocopheryl Acetate | 0.50 | Antioxidant, skin conditioning |
| MSM | 1.00 | Calming, soothing, masking |
| Strontium Chloride | 1.00 | Calming, soothing, masking |

TABLE 17-continued

Anti-aging face creams Retinol Charisma Delicate Instant Lift Retinol, 0.3%/1.0%/1.6%

| Ingredient | Concentration in final product [weigh %] | Main Functions |
| --- | --- | --- |
| Tween 20 | 0.20 | surfactant |
| Dermofeel ® PA-3 (sodium phytate + alcohol and water) | 0.10 | Chelating agent |
| Natrosol ™ 250 HR/HHR (hydroxyethylcellulose + sodium sulfate) | 0.20 | Bulking, emulsion stabilizing, viscosity controlling |
| Amido Betaine C (cocamidopropyl betaine, a concentrated coconut oil based amidopropyldimethyl-amino-betaine) | 0.20 | Bulking, masking |
| Glycerin | 3.50 | Humectant, masking |
| Jeemide ® MEAA (a 75% aqueous solution of the monethanolamide of acetic acid) | 3.00 | Humectant, antistatic agent, plasticizer and lubricant. |
| Gransil-SiW-7100 (methyl perfluorobutyl ether + isododecane + water + polysilicone-11 + butylene glycol + decyl glucoside) | 30.00 | A water-coated silicone elastomer dispersion for loading silicone elastomers into water-based formulations |
| Gransil ™ PSQ (Polymethylsilsesquioxane) | 5.00 | Aspherical powder designed that provides enhanced aesthetics to formulations, anti-wrinkle, anti-caking |
| β-White ™ (butylene glycol + hydrogenated lecithin + sodium oleate + Oligopeptide-68 + glycine soja oil + disodium EDTA) | 5.00 | A whitening peptide (decreases tyrosinase activity and melanin synthesis, Induces skin lightening effect) |
| Majestem ™ (derived from plant cell culture) | 5.00 | Anti-ageing: lifting, tightening the sagging neck skin, lifting the cheeks, smoothing |
| Tagravit ™ R1 (microcapsules containing Retinol (6-8%) + butylated hydroxytoluene + tricaprylin + polymethyl methacrylate) | 3.00 | Regenerating, revitalizing, lightening/whitening, and anti-wrinkle agent moisturizing and nourishing |
| Verstatil ® PC (caprylyl glycol + phenoxyethanol | 1.00 | Skin conditioning |
| ViscOptima ™ SE (sodium polyacrylate + ethylhexyl cocoate + PPG-3 benzyl ether myristate + polysorbate 20) | 0.5 | Multifunctional liquid rheology modifier that emulsifies and stabilizes high levels of oils and silicones within the formulation |
| AQUAXYL ™ (xylitylglucoside + anhydroxylitol + xylitol) | 2.00 | Moisturizing, stimulating the skin's natural production of hyaluronic acid |
| Water | 38.54/37.26/36.11 | Solvent |

TABLE 18

Physical/chemical characteristics of face cream Retinol Charisma Delicate Instant Lift Retinol, 0.3%

| Test | Specification | Units | Method |
| --- | --- | --- | --- |
| Appearance | Gel cream | — | Visual check |
| Odor | None | — | Organoleptic test |
| Color | Whitish to yellowish | — | Visual test |
| Density | 0-975-1.100 | g/ml | QC-F-03 |
| pH (at 25° C.) | 3.0-5.5 | — | QC-F-03 |

Example VII—Cleansers

Formulations disclosed herein, for skin cleaning, generally referred to herein as "cleansers" or "soaps", comprise a contemplated composition comprising a combination of MSM and strontium, and one or more active agents such as, but not limited to, myristic acid, sodium laureth sulfate, and disodium laureth sulfosuccinate, and the floral water of flowers of *Chamomilla recutita*, produced by distillation (e.g., medxtract Chamomile distilled).

A Cleanser Solution

A skin care cleansing solution, for deep cleaning, removal of excess oils and clearing surface impurities for pure, soft and supple skin, was prepared using the ingredients listed in Table 21. This formulation is referred to herein as "COSMO clear cleanser".

TABLE 19

COSMO clear cleanser

| Ingredient | Concentration in final product [weigh %] | Main Functions |
|---|---|---|
| Sodium laureth sulfate | 23.00 | Cleansing |
| Disodium laureth sulfosuccinate | 10.00 | Cleansing, foam boosting, surfactant |
| Medxtract chamomile distilled (*Chamomilla recutita* flower water) | 5.00 | Masking, perfuming, anticorrosive, preservative |
| MSM | 0.10 | Calming, soothing, masking |
| Strontium Chloride | 0.10 | Calming, soothing, masking |
| Tween 20 | 0.20 | surfactant |
| Dermofeel ® PA-3 (sodium phytate + alcohol and water) | 0.10 | Chelating agent |
| Cocamide DEA (Coconut oil diethanolamine condensate) | 3.00 | Foam boosting, emulsion stabilizing |
| Amido Betaine C (Cocamidopropyl Betaine, a concentrated coconut oil based amidopropyldimethyl-amino-betaine) | 0.20 | Antistatic, cleansing, foam boosting |
| Glycerin | 3.00 | Humectant, masking |
| Sodium chloride | 1.00 | Bulking, masking |
| Glycoil acid | 0.25 | Buffering |
| Lactic acid cosmetic grade 88% | 0.5 | Buffering, humectant, skin conditioning |
| Verstatil ® PC (caprylyl glycol + phenoxyethanol) | 1.00 | Skin conditioning, emollient |
| Bergamot oil | 0.30 | Masking, perfuming |
| Parfum (limonene) | 0.62 | Perfuming, allergen |
| Water | 52 | Solvent |

The exemplary cleanser disclosed herein has been shown to be detoxifying and provide deep cleansing, fresh sensation and was suitable for all skin types.

Example VIII—Skin Soothing Formulations

Skin soothing formulations, also referred to herein as "skin calming formulations", are formulations useful in preparing the skin for various chemical treatments such as peeling, filling and laser application, preparing the skin to hair removal procedure and heat- or cold-treatment protocols. Skin calming formulations disclosed herein are further useful for treating or alleviating irritated and sensitized skin and erythema associated with various skin diseases and conditions such as, but not limited to, cracked and dry skin, burns, damaged skin due dramatic temperature and/or pH changes, atopic dermatitis, eczema, seborrhea, rosacea, psoriasis, neurogenic inflammations caused by various ingredients of skin treatment products, and otherwise unpleased and irritating sensations associated with exposure to irritating chemicals and topical therapeutic substances.

Pre-Peel Solution

An exemplary soothing product, herein designated "Pre-Peel Conditioner" has been prepared using a contemplated composition comprising a combination of MSM and strontium, and other ingredients such as those listed in Table 20. This soothing formulation is useful in preparing the skin for any treatment such as peeling, filler and laser. It prepares the skin for peeling treatments by degreasing the skin and assisting the peel agents to evenly spread and penetrate. Some Physical and chemical properties of Pre-Peel Conditioner are listed in Table 21.

TABLE 20

Pre-peel conditioner formulation

| Ingredient | Concentration in final product [weigh %] | Main Functions |
|---|---|---|
| Lactic acid cosmetic grade 88% | 16.0 | Skin conditioning, humectant |
| MSM | 5.0 | Skin conditioning |
| Strontium Chloride | 5.0 | Skin conditioning |
| Citric acid | 12.0 | Buffering, chelating masking |
| *Gaultheria procumbens* leaf extract (containing salicylic acid) | 14.0 | Skin conditioning, tonic |
| Ethanol | 43.0 | Solvent |
| Water | 5.0 | Solvent |

TABLE 21

Physical/chemical characteristics of Pre-peel conditioner formulation

| Test | Specification |
|---|---|
| Appearance | Liquid |
| Odor | Characteristic |
| Color | Beige |
| Density | 0.75-0.80 g/ml |
| pH (at 25° C.) | 0.4-0.7 |
| Stability (84 days at 40° C.) | Good: no separation to phases, no aggregates, no change of color and odor. |

While certain features of the disclosure have been illustrated and described herein, many modifications, substitutions, changes, and equivalents will now occur to those of ordinary skill in the art. It is, therefore, to be understood that the appended claims are intended to cover all such modifications and changes as fall within the true spirit of the disclosure.

What is claimed is:

1. A topical composition comprising a combination of: a strontium salt selected from the group consisting of strontium chloride, strontium acetate, strontium nitrate and strontium chloride hexahydrate; methylsulfonylmethane; and a physiologically acceptable carrier, wherein the strontium salt:MSM concentration ratio is in the range of from 5%:10% to 10%:5% w/w.

2. The composition of claim 1, wherein the strontium salt:MSM concentration ratio is 5%:10% w/w.

3. The topical composition of claim 1, wherein the strontium salt is strontium chloride hexahydrate.

4. A topical formulation comprising the composition of claim 1, and at least one active ingredient.

5. The topical formulation of claim 4, wherein the at least one additional active ingredient is an alpha hydroxy acid (AHA), a beta hydroxy acid (BHA), a retinoid, an alpha keto acid, a dicarboxylic acid, arbutin, benzoyl peroxide, resorcinol, hydroquinone, kojic acid, myristic acid, sodium laureth sulfate, disodium laureth sulfosuccinate, sulfur or Vitamin C.

6. The topical formulation of claim 5, formulated as a cosmetic or a therapeutic formulation.

7. The topical formulation of claim 6, comprising one or more of: (i) lactic acid, glycolic acid, mandelic acid, tartaric acid, malic acid, citric acid, salicylic acid, azelaic acid, pyruvic acid, and any combination thereof, in amount of from 0.1% to 70% w/w; (ii) benzoyl peroxide, sulfur, resorcinol, resorcinol monoacetate, and any combination thereof, in amount of from 0.1% to 20% w/w; (iii) vitamin C a derivatives thereof, and any combination thereof in an amount of from 0.1% to 40% w/w; (iv) hydroquinone in an amount of from 0.1% to 10% w/w; (v) alpha-arbutin, beta-arbutin, and any combination thereof, in an amount of from 0.1% to 30% w/w; (vi) kojic acid in an amount of from 0.1% to 10% w/w; (vii) a retinoid in an amount of from 0.1% to 20% w/w; or (viii) sodium laureth sulfate, disodium laureth sulfosuccinate, chamomile distilled, myristic acid and any combination thereof, in an amount of from 0.1% to 50% w/w.

8. The topical formulation of claim 7, formulated as a rejuvenating or peeling formulation, comprising at least one of: (i) lactic acid in an amount of from 10% to 20% w/w; (ii) glycolic acid in an amount of from 10% to 50% w/w; or (iii) salicylic acid in an amount of from 1% to 20% w/w.

9. The topical formulation of claim 7, formulated an anti-acne formulation, comprising at least one of: (i) azelaic acid in an amount of from 0.1% to 40% w/w, from 0.1% to 5% w/w, or from 10% to 30% w/w; (i) lactic acid in an amount of from 10% to 20% w/w, or from 11% to 15% w/w; (iii) benzoyl peroxide in an amount of from 0.1% to 20% w/w, from 1% to 10% w/w, or from 5% to 10% w/w; (iv) sulfur in an amount of from 0.1% to 20% w/w, from 1% to 10% w/w, or from 5.0% to 10% w/w); or (v) resorcinol or resorcinol monoacetate in an amount of from 0.1% to 20% w/w, from 1% to 10% w/w, or from 5% to 10% w/w.

10. The topical formulation of claim 7, formulated as a whitening or lightening formulation, comprising at least one of: (i) azelaic acid in an amount of from 0.1% to 30% w/w, form 0.1% to 5% w/w, or from 10% to 30% w/w; (ii) hydroquinone in an amount of from 0.1% to 10% w/w or from 1% to 5% w/w; (iii) vitamin C or a derivative thereof in an amount of from 0.1% to 40% w/w, from 10% to 30% w/w, or from 1% to 5% w/w; (iv) alpha-arbutin or beta-arbutin in an amount of from 0.1% to 30% w/w, from 1% to 20% w/w, from 1% to 5% w/w, or from 5% to 10% w/w; or (v) kojic acid in an amount of from 0.1% to 10% w/w, from 0.5% to 1.5% w/w, or from 1% to 5% w/w.

11. The topical formulation of claim 7, formulated as an anti-aging formulation, comprising a retinoid in an amount of from 0.1% to 20% w/w, from 0.1% to 1% w/w, from 0.5% to 2% or from 1% to 5% w/w.

12. The topical formulation of claim 7, formulated as a cleanser, comprising at least one of sodium laureth sulfate, disodium laureth sulfosuccinate or chamomile distilled, each in an amount of from 0.1% to 50% w/w, from 1% to 10% w/w, from 5% to 15%, or from 10% to 25% w/w.

13. A method of cosmetic or therapeutic treatment comprising administering to a subject in need thereof of the topical composition of claim 1.

14. The method of claim 13, for reducing the development, incidence and severity of irritation and erythema associated with at least one of: skin treatment products, skin irritant products, chemicals, neurogenic inflammations, change of temperature, or change of pH.

15. The method of claim 13, for treating a skin disease or condition which is at least one of atopic dermatitis, eczema, seborrhea, rosacea or psoriasis.

16. The method of claim 13, wherein the strontium salt:MSM concentration ratio in the composition is 5%:10% w/w.

17. A method for treating, or alleviating sensations, or conditions associated with at least one of: skin treatment products, skin irritant products, chemicals, neurogenic inflammations, change of temperature, or change of pH, the method comprising administering the composition of claim 1, such that the combination of strontium salt and MSM provides a synergistic effect with respect to treatment of the sensations, or conditions as compared to the effect provided by administering strontium salt and MSM each alone.

18. The method of claim 17, wherein a sensation, or condition is at least one of stinging, itching, burning, edema, or erythema.

* * * * *